United States Patent
Marino et al.

(10) Patent No.: US 9,980,715 B2
(45) Date of Patent: May 29, 2018

(54) ANCHOR DEVICES AND METHODS OF USE

(71) Applicants: James F. Marino, La Jolla, CA (US); Jamil Elbanna, San Diego, CA (US)

(72) Inventors: James F. Marino, La Jolla, CA (US); Jamil Elbanna, San Diego, CA (US)

(73) Assignee: Trinity Orthopedics, LLC, San Diego, CA (US)

( * ) Notice: Subject to any disclaimer, the term of this patent is extended or adjusted under 35 U.S.C. 154(b) by 459 days.

(21) Appl. No.: 14/615,278

(22) Filed: Feb. 5, 2015

(65) Prior Publication Data

US 2015/0216523 A1 Aug. 6, 2015

Related U.S. Application Data

(60) Provisional application No. 61/936,153, filed on Feb. 5, 2014.

(51) Int. Cl.
| | |
|---|---|
| *A61B 17/04* | (2006.01) |
| *A61F 2/08* | (2006.01) |
| *A61B 17/00* | (2006.01) |

(52) U.S. Cl.
CPC ........ *A61B 17/0401* (2013.01); *A61F 2/0811* (2013.01); *A61B 2017/00986* (2013.01); *A61B 2017/0403* (2013.01); *A61B 2017/0438* (2013.01); *A61B 2017/0446* (2013.01); *A61B 2017/0454* (2013.01); *A61F 2002/0835* (2013.01); *A61F 2002/0864* (2013.01); *A61F 2002/0888* (2013.01)

(58) Field of Classification Search
CPC ........ A61B 17/0401; A61B 2017/0438; A61B 2017/0454; A61B 2017/0403; A61B 2017/0446; A61B 2017/00986; A61F 2/0811; A61F 2002/0888; A61F 2002/0864; A61F 2002/0835
See application file for complete search history.

(56) References Cited

U.S. PATENT DOCUMENTS

| | | | |
|---|---|---|---|
| 3,108,593 | A | 10/1963 | Glassman |
| 3,800,788 | A | 4/1974 | White |
| | | (Continued) | |

FOREIGN PATENT DOCUMENTS

| | | | |
|---|---|---|---|
| DE | 3840466 A1 | 6/1990 | |
| DE | 3922044 A1 | 2/1991 | |
| | (Continued) | | |

*Primary Examiner* — Son Dang
(74) *Attorney, Agent, or Firm* — Mintz Levin Cohn Ferris Glovsky and Popeo, P.C.

(57) ABSTRACT

An anchor device for attaching materials within bone including a body having a distal end region, a proximal end region, and a plurality of struts extending between the distal end region to the proximal end region and at least partially surrounding an interior volume of the body. The anchor device includes an attachment feature positioned within the interior volume of the body and coupled near the distal end region. The attachment feature is configured to secure material to the body. Upon removal of a constraint and after delivery of the anchor device into bone, the body passively transitions from a constrained, delivery configuration that is radially contracted and axially elongated to a relaxed, deployment configuration that is radially expanded and axially shortened.

24 Claims, 18 Drawing Sheets

(56) References Cited

U.S. PATENT DOCUMENTS

| | | |
|---|---|---|
| 3,846,846 A | 11/1974 | Fischer |
| 3,867,728 A | 2/1975 | Stubstad et al. |
| 4,475,856 A | 10/1984 | Toomingas |
| 4,750,492 A | 6/1988 | Jacobs |
| 4,898,156 A | 2/1990 | Gatturna et al. |
| 4,899,743 A | 2/1990 | Nicholson et al. |
| 4,946,468 A | 8/1990 | Li |
| 4,968,315 A | 11/1990 | Gatturna |
| 4,973,301 A | 11/1990 | Nissenkorn |
| 5,002,550 A | 3/1991 | Li |
| 5,046,513 A | 9/1991 | Gatturna et al. |
| 5,059,193 A * | 10/1991 | Kuslich ............... F16B 13/061 606/247 |
| 5,062,845 A | 11/1991 | Kuslich et al. |
| 5,108,395 A | 4/1992 | Laurain |
| 5,123,926 A | 6/1992 | Pisharodi |
| 5,167,665 A | 12/1992 | McKinney |
| 5,171,248 A | 12/1992 | Ellis |
| 5,171,278 A | 12/1992 | Pisharodi |
| 5,192,303 A | 3/1993 | Gatturna et al. |
| 5,207,679 A | 5/1993 | Li |
| 5,217,486 A | 6/1993 | Rice et al. |
| 5,263,953 A | 11/1993 | Bagby |
| 5,275,608 A | 1/1994 | Forman et al. |
| 5,306,310 A | 4/1994 | Siebels |
| 5,356,413 A | 10/1994 | Martins et al. |
| 5,358,511 A | 10/1994 | Gatturna et al. |
| 5,372,599 A | 12/1994 | Martins |
| 5,390,683 A | 2/1995 | Pisharodi |
| 5,402,772 A | 4/1995 | Moll et al. |
| 5,417,712 A | 5/1995 | Whittaker et al. |
| 5,454,365 A | 10/1995 | Bonutti |
| 5,456,667 A | 10/1995 | Ham et al. |
| 5,501,695 A * | 3/1996 | Anspach, Jr. ...... A61B 17/0401 411/34 |
| 5,505,735 A | 4/1996 | Li |
| 5,518,498 A | 5/1996 | Lindenberg et al. |
| 5,522,845 A | 6/1996 | Wenstrom, Jr. |
| 5,549,679 A | 8/1996 | Kuslich |
| 5,554,171 A | 9/1996 | Gatturna et al. |
| 5,569,306 A | 10/1996 | Thal |
| 5,571,104 A | 11/1996 | Li |
| 5,571,189 A | 11/1996 | Kuslich |
| 5,575,790 A | 11/1996 | Chen et al. |
| 5,578,035 A | 11/1996 | Lin |
| 5,591,197 A | 1/1997 | Orth et al. |
| 5,658,313 A | 8/1997 | Thal |
| 5,665,112 A | 9/1997 | Thal |
| 5,683,419 A | 11/1997 | Thal |
| 5,702,448 A | 12/1997 | Buechel et al. |
| 5,720,765 A | 2/1998 | Thal |
| 5,725,341 A | 3/1998 | Hofmeister |
| 5,725,557 A | 3/1998 | Gatturna et al. |
| 5,728,136 A | 3/1998 | Thal |
| 5,741,282 A * | 4/1998 | Anspach, III ...... A61B 17/0401 606/151 |
| 5,749,916 A | 5/1998 | Richelsoph |
| 5,759,186 A | 6/1998 | Bachmann et al. |
| 5,782,832 A | 7/1998 | Larsen et al. |
| 5,782,838 A | 7/1998 | Beyar et al. |
| 5,782,864 A | 7/1998 | Lizardi |
| 5,827,289 A | 10/1998 | Reiley et al. |
| 5,843,158 A | 12/1998 | Lenker et al. |
| 5,853,422 A * | 12/1998 | Huebsch ............ A61B 17/0057 606/157 |
| 5,876,457 A | 3/1999 | Picha et al. |
| 5,885,294 A | 3/1999 | Pedlick et al. |
| 5,897,557 A | 4/1999 | Chin et al. |
| 5,935,134 A | 8/1999 | Pedlick et al. |
| 5,972,015 A | 10/1999 | Scribner et al. |
| 5,976,187 A | 11/1999 | Richelsoph |
| 5,989,291 A | 11/1999 | Ralph et al. |
| 6,019,789 A | 2/2000 | Dinh et al. |
| 6,019,793 A | 2/2000 | Perren et al. |
| 6,024,758 A | 2/2000 | Thal |
| 6,039,761 A | 3/2000 | Li et al. |
| 6,041,485 A | 3/2000 | Pedlick et al. |
| 6,056,749 A | 5/2000 | Kuslich |
| 6,086,589 A | 7/2000 | Kuslich et al. |
| 6,126,689 A | 10/2000 | Brett |
| 6,127,597 A | 10/2000 | Beyar et al. |
| 6,143,017 A | 11/2000 | Thal |
| 6,149,651 A | 11/2000 | Drewry et al. |
| 6,149,669 A * | 11/2000 | Li ...................... A61B 17/0401 606/232 |
| 6,156,039 A | 12/2000 | Thal |
| 6,193,757 B1 | 2/2001 | Foley et al. |
| 6,200,349 B1 | 3/2001 | Naybour |
| 6,206,923 B1 | 3/2001 | Boyd et al. |
| 6,214,037 B1 | 4/2001 | Mitchell et al. |
| 6,217,608 B1 | 4/2001 | Penn et al. |
| 6,224,604 B1 | 5/2001 | Suddaby |
| 6,245,101 B1 | 6/2001 | Drasler et al. |
| 6,248,110 B1 | 6/2001 | Reiley et al. |
| 6,261,289 B1 | 7/2001 | Levy |
| 6,287,324 B1 | 9/2001 | Yarnitsky et al. |
| 6,328,758 B1 | 12/2001 | Tornier et al. |
| 6,383,188 B2 | 5/2002 | Kuslich et al. |
| 6,395,031 B1 | 5/2002 | Foley et al. |
| 6,409,766 B1 | 6/2002 | Brett |
| 6,440,138 B1 | 8/2002 | Reiley et al. |
| 6,447,478 B1 | 9/2002 | Maynard |
| 6,488,710 B2 | 12/2002 | Besselink |
| 6,500,182 B2 | 12/2002 | Foster |
| 6,551,319 B2 | 4/2003 | Lieberman |
| 6,554,833 B2 | 4/2003 | Levy et al. |
| 6,562,074 B2 | 5/2003 | Gerbec et al. |
| 6,582,453 B1 * | 6/2003 | Tran ................... A61B 17/0401 606/232 |
| 6,582,467 B1 | 6/2003 | Teitelbaum et al. |
| 6,620,162 B2 | 9/2003 | Kuslich et al. |
| 6,620,169 B1 | 9/2003 | Peterson et al. |
| 6,641,596 B1 | 11/2003 | Lizardi |
| 6,660,008 B1 * | 12/2003 | Foerster ............. A61B 17/0401 411/34 |
| 6,666,891 B2 | 12/2003 | Boehm, Jr. et al. |
| 6,676,665 B2 | 1/2004 | Foley et al. |
| 6,679,886 B2 | 1/2004 | Weikel et al. |
| 6,712,853 B2 | 3/2004 | Kuslich |
| 6,740,090 B1 | 5/2004 | Cragg et al. |
| 6,773,460 B2 | 8/2004 | Jackson |
| 6,780,175 B1 | 8/2004 | Sachdeva et al. |
| 6,833,006 B2 | 12/2004 | Foley et al. |
| 6,893,464 B2 | 5/2005 | Kiester |
| 6,923,813 B2 | 8/2005 | Phillips et al. |
| 6,932,834 B2 | 8/2005 | Lizardi et al. |
| 6,960,215 B2 | 11/2005 | Olson, Jr. et al. |
| 6,962,606 B2 | 11/2005 | Michelson |
| 6,969,404 B2 | 11/2005 | Ferree |
| 7,052,498 B2 | 5/2006 | Levy et al. |
| 7,070,598 B2 | 7/2006 | Lim et al. |
| 7,083,650 B2 | 8/2006 | Moskowitz et al. |
| 7,087,055 B2 | 8/2006 | Lim et al. |
| 7,097,648 B1 | 8/2006 | Globerman et al. |
| 7,128,760 B2 | 10/2006 | Michelson |
| 7,144,415 B2 * | 12/2006 | Del Rio .............. A61B 17/0401 606/232 |
| 7,166,121 B2 | 1/2007 | Reiley et al. |
| 7,189,235 B2 | 3/2007 | Cauthen |
| 7,211,073 B2 | 5/2007 | Fitzgerald et al. |
| 7,214,243 B2 | 5/2007 | Taylor |
| 7,217,293 B2 | 5/2007 | Branch, Jr. |
| 7,297,146 B2 | 11/2007 | Braun et al. |
| 7,381,213 B2 | 6/2008 | Lizardi |
| 7,452,351 B2 | 11/2008 | Miller et al. |
| 7,585,311 B2 | 9/2009 | Green et al. |
| 7,655,042 B2 | 2/2010 | Foley et al. |
| 7,722,674 B1 | 5/2010 | Grotz |
| 7,766,939 B2 | 8/2010 | Yeung et al. |
| 7,819,921 B2 | 10/2010 | Grotz |
| 7,892,286 B2 | 2/2011 | Michelson |
| 7,963,970 B2 | 6/2011 | Marino |
| 7,985,256 B2 | 7/2011 | Grotz et al. |
| 7,993,403 B2 | 8/2011 | Foley et al. |

(56) References Cited

U.S. PATENT DOCUMENTS

| | | | |
|---|---|---|---|
| 8,043,376 B2 | 10/2011 | Falahee | |
| 8,070,813 B2 | 12/2011 | Grotz et al. | |
| 8,105,382 B2 | 1/2012 | Olmos et al. | |
| 8,123,807 B2 | 2/2012 | Kim | |
| 8,236,058 B2 | 8/2012 | Fabian et al. | |
| 8,435,264 B2 | 5/2013 | Sojka et al. | |
| 8,435,294 B2 | 5/2013 | Montgomery et al. | |
| 8,454,654 B2 | 6/2013 | Ferragamo et al. | |
| 8,454,655 B2 | 6/2013 | Yeung et al. | |
| 8,454,695 B2 | 6/2013 | Grotz et al. | |
| 8,460,340 B2 | 6/2013 | Sojka et al. | |
| 8,469,998 B2 | 6/2013 | Sojka et al. | |
| 8,529,628 B2 | 9/2013 | Marino et al. | |
| 8,882,787 B2* | 11/2014 | Brenzel | A61B 19/54 604/107 |
| 9,226,742 B2* | 1/2016 | Wolf | A61B 17/0401 |
| 2002/0026197 A1 | 2/2002 | Foley et al. | |
| 2002/0055738 A1 | 5/2002 | Lieberman | |
| 2002/0072768 A1* | 6/2002 | Ginn | A61B 17/0057 606/213 |
| 2003/0074075 A1 | 4/2003 | Thomas et al. | |
| 2003/0083746 A1 | 5/2003 | Kuslich | |
| 2003/0088250 A1 | 5/2003 | Colleran et al. | |
| 2003/0195564 A1 | 10/2003 | Tran et al. | |
| 2004/0010315 A1 | 1/2004 | Song | |
| 2004/0097930 A1 | 5/2004 | Justis et al. | |
| 2004/0138707 A1 | 7/2004 | Greenhalgh | |
| 2004/0153064 A1 | 8/2004 | Foley et al. | |
| 2004/0193158 A1 | 9/2004 | Lim et al. | |
| 2004/0220577 A1 | 11/2004 | Cragg et al. | |
| 2005/0038447 A1 | 2/2005 | Huffmaster | |
| 2005/0060023 A1 | 3/2005 | Mitchell et al. | |
| 2005/0113836 A1 | 5/2005 | Lozier et al. | |
| 2005/0113838 A1 | 5/2005 | Phillips et al. | |
| 2005/0119675 A1* | 6/2005 | Adams | A61B 17/0057 606/151 |
| 2005/0131417 A1 | 6/2005 | Ahern et al. | |
| 2005/0143827 A1 | 6/2005 | Globerman et al. | |
| 2005/0182417 A1 | 8/2005 | Pagano | |
| 2005/0197711 A1 | 9/2005 | Cachia | |
| 2005/0222681 A1 | 10/2005 | Richley et al. | |
| 2005/0251209 A1* | 11/2005 | Saadat | A61B 17/0401 606/232 |
| 2005/0273135 A1* | 12/2005 | Chanduszko | A61B 17/0057 606/213 |
| 2005/0277983 A1* | 12/2005 | Saadat | A61B 17/0401 606/215 |
| 2006/0009844 A1 | 1/2006 | Bloemer et al. | |
| 2006/0036323 A1 | 2/2006 | Carl et al. | |
| 2006/0064094 A1 | 3/2006 | Levy et al. | |
| 2006/0074422 A1 | 4/2006 | Story et al. | |
| 2006/0084985 A1 | 4/2006 | Kim | |
| 2006/0084998 A1 | 4/2006 | Levy et al. | |
| 2006/0100706 A1 | 5/2006 | Shadduck et al. | |
| 2006/0122647 A1* | 6/2006 | Callaghan | A61B 17/0057 606/213 |
| 2006/0136065 A1 | 6/2006 | Gontarz et al. | |
| 2006/0155379 A1 | 7/2006 | Heneveld et al. | |
| 2006/0167547 A1 | 7/2006 | Suddaby | |
| 2006/0235417 A1 | 10/2006 | Sala | |
| 2006/0271061 A1 | 11/2006 | Beyar et al. | |
| 2006/0271197 A1 | 11/2006 | Saal et al. | |
| 2006/0282081 A1* | 12/2006 | Fanton | A61B 17/0401 606/232 |
| 2007/0038221 A1 | 2/2007 | Fine et al. | |
| 2007/0043373 A1 | 2/2007 | Sala et al. | |
| 2007/0043440 A1 | 2/2007 | William et al. | |
| 2007/0050033 A1 | 3/2007 | Reo et al. | |
| 2007/0067034 A1 | 3/2007 | Chirico et al. | |
| 2007/0088436 A1 | 4/2007 | Parsons et al. | |
| 2007/0118171 A1 | 5/2007 | Reiley et al. | |
| 2007/0118222 A1 | 5/2007 | Lang | |
| 2007/0142838 A1 | 6/2007 | Jordan | |
| 2007/0150063 A1 | 6/2007 | Ruberte et al. | |
| 2007/0162044 A1 | 7/2007 | Marino | |
| 2007/0162127 A1 | 7/2007 | Peterman et al. | |
| 2007/0173939 A1 | 7/2007 | Kim et al. | |
| 2007/0198013 A1 | 8/2007 | Foley et al. | |
| 2007/0198088 A1 | 8/2007 | Biedermann et al. | |
| 2007/0219634 A1 | 9/2007 | Greenhalgh et al. | |
| 2007/0270959 A1 | 11/2007 | Dubousset | |
| 2007/0282443 A1 | 12/2007 | Globerman et al. | |
| 2007/0293866 A1 | 12/2007 | Stoeckel et al. | |
| 2008/0009875 A1 | 1/2008 | Sankaran et al. | |
| 2008/0009876 A1 | 1/2008 | Sankaran et al. | |
| 2008/0009877 A1 | 1/2008 | Sankaran et al. | |
| 2008/0065143 A1 | 3/2008 | Reiley et al. | |
| 2008/0071356 A1 | 3/2008 | Greenhalgh et al. | |
| 2008/0086212 A1 | 4/2008 | Zucherman et al. | |
| 2008/0114367 A1 | 5/2008 | Meyer | |
| 2008/0140203 A1 | 6/2008 | Davis | |
| 2008/0147192 A1 | 6/2008 | Edidin et al. | |
| 2008/0147194 A1 | 6/2008 | Grotz et al. | |
| 2008/0154305 A1 | 6/2008 | Foley et al. | |
| 2008/0161933 A1 | 7/2008 | Grotz et al. | |
| 2008/0183204 A1 | 7/2008 | Greenhalgh et al. | |
| 2008/0228028 A1 | 9/2008 | Carlson et al. | |
| 2008/0281364 A1* | 11/2008 | Chirico | A61B 17/025 606/86 A |
| 2008/0294204 A1* | 11/2008 | Chirico | A61F 2/0805 606/327 |
| 2009/0005821 A1 | 1/2009 | Chirico et al. | |
| 2009/0012564 A1 | 1/2009 | Chirico et al. | |
| 2009/0024157 A1 | 1/2009 | Anukhin | |
| 2009/0024166 A1 | 1/2009 | Carl et al. | |
| 2009/0036799 A1 | 2/2009 | Sandhu et al. | |
| 2009/0054935 A1 | 2/2009 | Miller et al. | |
| 2009/0125071 A1 | 5/2009 | Skinlo et al. | |
| 2009/0216331 A1 | 8/2009 | Grotz et al. | |
| 2009/0287246 A1 | 11/2009 | Cauldweli et al. | |
| 2009/0292313 A1* | 11/2009 | Anspach, III | A61B 17/0401 606/232 |
| 2009/0312764 A1 | 12/2009 | Marino | |
| 2010/0057204 A1 | 3/2010 | Kadaba et al. | |
| 2010/0121355 A1* | 5/2010 | Gittings | A61B 17/0401 606/148 |
| 2010/0145455 A1 | 6/2010 | Simpson et al. | |
| 2010/0145456 A1 | 6/2010 | Simpson et al. | |
| 2010/0152735 A1 | 6/2010 | Brown et al. | |
| 2010/0292732 A1 | 11/2010 | Hirotsuka et al. | |
| 2010/0292733 A1* | 11/2010 | Hendricksen | A61B 17/0401 606/232 |
| 2010/0305705 A1 | 12/2010 | Butler et al. | |
| 2011/0004242 A1 | 1/2011 | Stchur | |
| 2011/0009869 A1 | 1/2011 | Marino et al. | |
| 2011/0137420 A1 | 6/2011 | Michelson | |
| 2011/0224726 A1 | 9/2011 | Lombardo et al. | |
| 2011/0264140 A1 | 10/2011 | Lizardi et al. | |
| 2011/0313453 A1* | 12/2011 | Krumme | A61B 17/0401 606/232 |
| 2012/0041496 A1 | 2/2012 | Walker | |
| 2012/0053627 A1 | 3/2012 | Sojka et al. | |
| 2012/0053628 A1 | 3/2012 | Sojka et al. | |
| 2013/0072975 A1 | 3/2013 | Van Der Burg et al. | |
| 2013/0079818 A1 | 3/2013 | Lizardi et al. | |
| 2013/0085528 A1 | 4/2013 | DiMatteo et al. | |
| 2013/0158597 A1 | 6/2013 | Hernandez | |
| 2013/0158599 A1 | 6/2013 | Hester et al. | |
| 2013/0197578 A1* | 8/2013 | Gregoire | A61B 17/0401 606/232 |
| 2014/0046369 A1 | 2/2014 | Heaven et al. | |
| 2015/0005810 A1* | 1/2015 | Center | A61F 2/01 606/200 |
| 2015/0018878 A1 | 1/2015 | Rizk et al. | |

FOREIGN PATENT DOCUMENTS

| | | |
|---|---|---|
| DE | 10003331 A1 | 8/2001 |
| EP | 1529494 A1 | 5/2005 |
| EP | 1535579 A2 | 6/2005 |
| EP | 1748739 A1 | 2/2007 |
| FR | 2717068 A1 | 9/1995 |

(56) References Cited

FOREIGN PATENT DOCUMENTS

| | | |
|---|---|---|
| GB | 2268068 A | 1/1994 |
| WO | WO-00/44319 A1 | 8/2000 |
| WO | WO-02/43628 A1 | 6/2002 |
| WO | WO-2005/011507 A1 | 2/2005 |
| WO | WO-2005/048856 A1 | 6/2005 |
| WO | WO-2005/110259 A1 | 11/2005 |
| WO | WO-2006/016384 A1 | 2/2006 |
| WO | WO-2007/003243 A1 | 1/2007 |
| WO | WO-2007/034516 A1 | 3/2007 |
| WO | WO-2007/113862 A1 | 10/2007 |
| WO | WO-2008/024563 A2 | 2/2008 |
| WO | WO-2009/143496 A1 | 11/2009 |
| WO | WO-2009/152256 A2 | 12/2009 |
| WO | WO-2010/078488 A2 | 7/2010 |
| WO | WO-2012/135141 A2 | 10/2012 |
| WO | WO-2014/150053 A1 | 9/2014 |

\* cited by examiner

ANCHOR DEVICES AND METHODS OF USE

CROSS-REFERENCE TO RELATED APPLICATIONS

This application claims priority of U.S. Provisional Patent Application Ser. No. 61/936,153, entitled "ANCHOR DEVICES AND METHODS OF USE" and was filed on Feb. 5, 2014. This disclosure of the provisional patent application is hereby incorporated by reference in its entirety.

BACKGROUND

In orthopedic surgical procedures, surgeons attach or reattach soft tissue structures to bone using anchor devices. Difficulties can arise due overly complicated anchor devices and time consuming procedures to implant that can still ultimately result in failure of the attachment.

SUMMARY

The present disclosure relates to methods, systems and devices to rapidly, easily and reliably anchor sutures or soft tissues such as tendon, ligament or joint capsule to bone.

In an implementation, disclosed is an anchor device for attaching materials within bone including a body having a distal end region, a proximal end region, and a plurality of struts extending between the distal end region to the proximal end region and at least partially surrounding an interior volume of the body. The anchor device includes an attachment feature positioned within the interior volume of the body and coupled near the distal end region. The attachment feature is configured to secure material to the body. Upon removal of a constraint and after delivery of the anchor device into bone, the body passively transitions from a constrained, delivery configuration that is radially contracted and axially elongated to a relaxed, deployment configuration that is radially expanded and axially shortened.

The material secured by the attachment feature to the anchor device can be suture or cable material. The material can be further affixed to a soft tissue structure such as tendon, ligament, and joint capsule. The attachment feature can include a suture anchor element, a cleat element, a post, a saddle-shaped element, a pulley, or a crimping element. The attachment feature can include a post extending transverse to the longitudinal axis of the body. The attachment feature can include a saddle shaped element to which the material is secured. The attachment feature can include a cleat element to secure the material. The cleat element can employ a cam action or ratcheting reel assembly to progressively tension the material and approximate the material to the proximal end region of the body. The cleat element can include at least one suture anchor element, two apertures and an intervening central post. A first portion of the material can overlap a second portion of the material resulting in a unidirectional tensioning mechanism of the material with the cleat element. The cleat element can include at least two suture anchor elements, each having an aperture configured to allow the material to extend through. Applying tension to the material can force the at least two suture anchor elements to form a splayed configuration. The tension applied to the material can be maintained by the at least two suture anchor elements. At least a part of the material passed through the apertures of the at least two suture anchor elements and wrapped around the commonly formed post can result in a portion of the material overlapping another portion of the material. The attachment feature can include a crimping element to secure the material, wherein the material is attached to a soft tissue structure. The material can be secured with an interference pin delivered through an opening in the proximal end region of the body. A proximal aspect of the crimping element can include a cable or suture transecting feature.

The device can further include a penetrating tip coupled to the distal end region of the body. The penetrating tip can have a trephine, fluted or conically-tapered outer geometry to facilitate penetration of bone. The material can include a tensioning element configured to approximate the distal end region and the proximal end region upon application of tension on the material causing the plurality of struts to radially expand. The penetrating tip and the tensioning element can be integrated with the attachment feature forming an inner body extending within the internal volume and surrounded at least in part by the body.

The proximal end region can include a discontinuous outer wall defining a proximal opening to the interior volume of the body within which the material is disposed such that soft tissue affixed to the material is in direct contact with the bone. The plurality of struts can expand near the proximal end region to a greater degree than the plurality of struts expand near the distal end region. The body can be fabricated from a superelastic metal. The constraint can include a generally rigid tubular element. The generally rigid tubular element can include a slot to accommodate the material. The constraint can include a circumferential ring element. The circumferential ring element can be positioned between the material and the bone thereby preventing abrasion of the material. The material can include suture, cable or soft tissue. The constraint can include a primary constraint and a secondary constraint. The secondary constraint can be positioned over at least a region of the primary constraint during storage of the anchor device.

In an interrelated aspect, described is a suture or soft tissue anchor device including a self-expanding device configured to be constrained prior to delivery having a relatively reduced diameter with a relatively extended length, and subsequently expanded to a relatively larger diameter with a relatively shortened length after deployment and delivery within bone. The self-expanding device can include a generally cylindrical or truncated cylindrical shaped body having two or more slots configured to be constrained prior to delivery.

In an interrelated aspect, described is a suture or soft tissue anchor device configured to employ a self-expanding device that is constrained prior to delivery, in a relatively reduced diameter and relatively extended length, with subsequent deployment and delivery within bone, where it is configured to expand to a relatively larger diameter with a relatively shortened length; in which suture material or cable attached to the soft tissue being approximated or secured to the bone anchor is affixed or otherwise associated with the distal terminus or an element associated with the distal terminus of the anchor.

In an interrelated aspect, described is a suture or soft tissue anchor device configured to employ a self-expanding device that is constrained prior to delivery, in a relatively reduced diameter and relatively extended length, with subsequent deployment and delivery within bone, where it expands to a relatively larger diameter with a relatively shortened length; in which suture material or cable attached to the soft tissue being approximated or secured to the bone anchor is affixed or otherwise associated with the distal terminus or an element associated with the distal terminus of the anchor, such that tension applied on the suture or cable results in a force that foreshortens the length and expands the diameter of the anchor.

The device can be fabricated at least in part from a superelastic metal. The superelastic metal can be nitinol. A suture affixed to a soft tissue structure can be secured to the distal end of the self-expanding implant. The soft tissue structure can be a tendon, ligament, or joint capsule. The self-expanding device can be further expanded by means of a tensioning element that approximates the distal and proximal ends of the device. The device can further include a distal tip that is conically tapered to facilitate penetration of bone. The distal tip can be configured with trephine or fluted geometry to facilitate penetration of bone. Suture affixed to a soft tissue structure can be passed through an aperture located distally within the device and delivered through the proximal aperture of the device for subsequent tensioning. A cam action cleat mechanism can be used to progressively tension the sutures and approximate the attached soft tissue element to the proximal aspect of the self-expanding device. A ratcheting reel assembly can be used to tension the sutures and approximate the attached soft tissue structure to the proximal aspect of the self-expanding device. The sutures coursing within the device and attached to a soft tissue structure can be secured to the device with a crimping element. The proximal aspect of the crimping mechanism can include a cable or suture transecting feature. The sutures coursing within the device and attached to a soft tissue structure can be secured with an interference pin, delivered within the proximal aperture. The interference pin can have a tapered distal tip. The cable or sutures restrained by the interference pin can be transected immediately proximal or adjacent to the proximal aspect of the interference pin with a cable or suture cutter having a rotary actuation mechanism.

A generally tubular configured confinement element can be used to maintain the self-expanding device in its confined geometry prior to distal delivery out of the confinement tube and into the bone. The primary confinement tube can have a slot to accommodate introduction of suture material attached to a soft tissue structure. A secondary confinement tubing or ring element can be positioned over the distal segment of the primary confinement tube during storage and removed after chilling the self-expanding device immediately or shortly prior to deployment within the bone. A secondary confinement tubing can be positioned over the distal segment of the primary confinement tube during storage and removed after chilling the self-expanding device immediately or shortly prior to deployment within the bone. The device can include at least one suture anchor element having two apertures and an intervening central post, to allow suture to extend through the apertures and around the central post such that a portion of the suture overlaps another portion of the suture, resulting in a unidirectional tensioning mechanism of the suture or cleat mechanism. The device can employ a cam action cleat mechanism to progressively tension the sutures and approximate the attached soft tissue element to the proximal aspect of the self-expanding device. The unidirectional tensioning mechanism can include at least two suture anchor elements. Each can have an aperture and a commonly formed post including at least one post element from each of the at least two suture anchor elements. The suture can be passed through the apertures of the at least two suture anchor elements and wrapped around the common post. The device can include at least two suture anchor elements, each having an aperture configured to allow suture to extend through. Applying tension to the suture can force the at least two suture anchor elements to form a splayed configuration. The tension applied to the suture can be maintained by the at least two suture anchor elements. At least a part of the suture passed through the apertures of the at least two suture anchor elements and wrapped around the commonly formed post can result in a portion of the suture overlapping another portion of the same suture.

In an interrelated aspect, described is a self-expanding suture anchor device including a pre-deployment confined configuration which is at least in part maintained by a circumferential ring element, which in the deployed state of the suture anchor device, serves to provide a suture abrasion protective function resulting from its surface features and deployment position, located between the suture material and the bone.

In an interrelated aspect, described is an anchor device for attaching tissue within bone. The device includes a body having a distal end region, a proximal end region, and a plurality of struts extending between the distal end region to the proximal end region and at least partially surround an interior volume of the body. The body passively transitions from a constrained, delivery configuration that is radially contracted and axially elongated to a relaxed, deployment configuration that is radially expanded and axially shortened upon removal of a constraint on the plurality of struts after delivery into bone. The device includes an attachment feature positioned within the interior volume of the body near the distal end region. The attachment feature is configured to secure the tissue to the anchor device. The device includes a distal penetrating tip. The proximal end region includes a discontinuous outer wall defining a proximal opening to the interior volume of the body within which the secured tissue is disposed so as to be in direct contact with the bone.

In an interrelated aspect, described is a method for anchoring soft tissue including constraining a self-expanding anchor device within a lumen of a constraining element. The self-expanding anchor device includes a plurality of struts extending between a distal end region and a proximal end region of the anchor device and at least partially surrounding an internal volume of the anchor device. The self-expanding anchor device includes an attachment feature positioned near the distal end region of the anchor device; and a proximal opening into the internal volume. At least a portion of the plurality of struts are constrained by the constraining element and at least a portion of the distal end region extends beyond a distal edge of the constraining element. The method includes securing a material to the attachment feature and routing the material through the internal volume of the anchor device. The method includes penetrating a bone surface with the distal end region of the self-expanding anchor device until the distal edge of the constraining element abuts the bone surface. The method includes sliding an advancing element relative to the constraining element urging the anchor device beyond the distal end of the constraining element into a subcortical location of the bone surface. The method includes passively expanding the plurality of struts within the subcortical location. The material can be suture or cable or soft tissue or can be suture or cable secured to soft tissue. The method can further include constraining the device to a constrained configuration at ambient storage temperatures by the constraining element. The method can further include chilling the device immediately prior to delivery into the body and removing the constraining element after chilling the device.

In an interrelated aspect, described is an implantable fixation device formed at least in part of temperature affected shape set material that transitions from a geometrically confined configuration to an expanded configuration. The device is constrained to the confined configuration at ambient storage temperatures by a removable element. The removable element is removed after the temperature affected shape set material is chilled immediately prior to delivery into the body. The removable element can be generally tubular. A secondary confinement tubing or ring element can be positioned over a distal segment of the removable element during storage. The secondary confinement tubing can be removed after chilling the self-expanding device immediately or shortly prior to deployment within the bone. The implantable fixation device can be an implantable soft tissue fixation device.

The above-noted aspects and features may be implemented in systems, apparatus, and/or methods, depending on the desired configuration. The details of one or more variations of the subject matter described herein are set forth in the accompanying drawings and the description below. Features and advantages of the subject matter described herein will be apparent from the description and drawings, and from the claims.

BRIEF DESCRIPTION OF THE DRAWINGS

Reference is made to the following description, taken in conjunction with the accompanying drawings, in which like reference characters refer to like parts throughout.

It is to be understood that implants described herein may include features not necessarily depicted in each figure.

DETAILED DESCRIPTION

During at least some orthopedic surgical procedures, surgeons can attach or reattach soft tissue structures to bone via suture material. A suture anchor device can provide a way for anchoring to the bone, such as cortical or cortical cancellous fixation. Fixation can be provided by an implant having interference fit or a thread form. Alternatively, fixation of the implant can be achieved by radial expansion within the subcortical cancellous bone. The expansion can occur beyond the cortical defect through which the implant was inserted such that pull-out of the implant is resisted.

Described herein are devices, systems and methods of use to provide a rapid, easy and reliable way to anchor sutures or soft tissues such as tendon, ligament or joint capsule to bone. The anchor devices described herein are simple to deploy in that they are self-expanding and, while still possible, do not require active expansion. The anchor devices described herein allow for better vascular growth and more surface fixation. The anchor devices described herein prevent the strangulation of the soft tissue to be affixed or the trapping of the soft tissue between rigid parts of the anchor device or the bone channel. The anchor devices described herein can cradle the soft tissue to be affixed within the interior volume of the device while still allowing for direct intimate contact of the soft tissue with the bone to which it is being affixed thereby promoting bone and soft-tissue attachment to the secured tissue.

Figure 1:
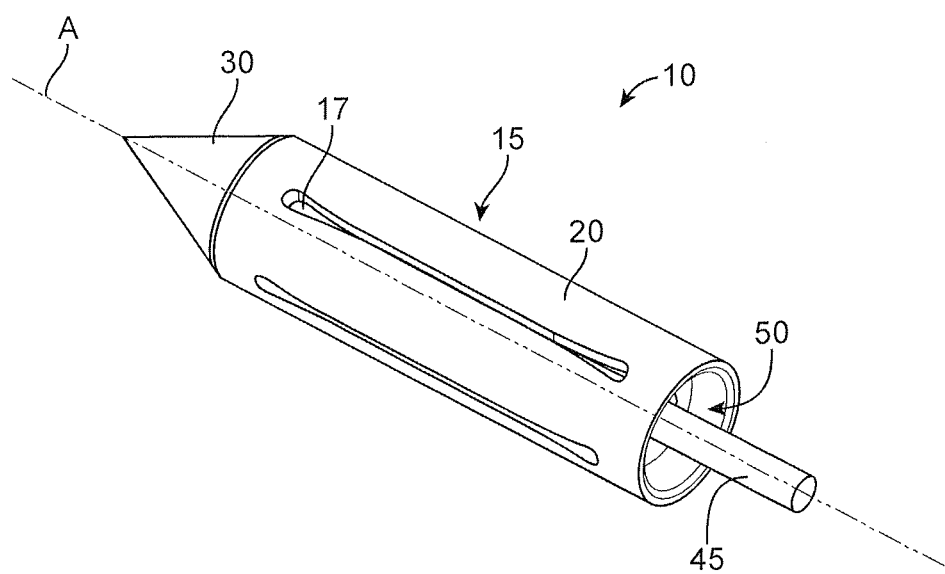
FIG. 1 shows a perspective view of an implementation of an anchor device in an unexpanded state.

FIG. 1 shows an implementation of an anchor device 10. The anchor device 10 can be configured to anchor suture to bone. The anchor device 10 can include a cylindrical outer body 15 having a plurality of slots 17 forming a plurality of stays or struts 20. The anchor device 10 can include two or more longitudinally extending slots 17 along its long axis A and on its tubular outer body 15 that can define the edges or margins of the deployable struts 20. The struts 20 can be located along the central portion of the generally tubular portion of the anchor device 10. The tubular outer body 15 can be coupled to an inner element 25 having a piercing distal tip 30. The distal tip 30 can be pointed or conically tapered to facilitate penetration of bone. The distal tip 30 can be configured with trephine or fluted geometry to facilitate penetration of bone. It should be appreciated that the distal tip 30 need not be integrated with the inner element 25 and can be coupled to a distal end region of the outer body 15 according to other configuration.

In some implementations, the anchor device 10 can have a long axis A, defining a generally tubular or cylindrical body geometry to the anchor device 10 immediately prior to insertion and delivery. The long axis A can have a proximal end that can be superficial in location and a distal end that can be deep in location with respect to the patient's bone surface or cortex. The proximal end of the anchor device 10 can be tapped such as with or through a deployment tool to force the sharp distal tip 30 through bone material. The proximal end of the anchor device 10 can also be pushed to urged the anchor device 10 through a pre-drilled hole.

In some implementations, the outer body 15 of the anchor device 10 can be self-expanding. The outer body 15 can be fabricated from super-elastic shape memory metal, such as Nitinol. Prior to deployment, the struts 20 of the outer body 15 can be constrained by an implant deployment tool (for example, like the tool 800 shown in FIG. 8) such that the plurality of struts 20 are constrained into a first configuration having a reduced diameter geometry, for example prior to delivery into bone. The plurality of struts 20 can also be configured to expand to a second configuration having an enlarged diameter geometry upon removal of the constraint after delivery in the bone. The deployment tool 800 can include a constraining element 810 such as an external tube having a distal wall slot 814 (see FIG. 4B) to accommodate suture delivery and suture deployment tensioning as will be described in more detail below. Upon deployment, the superelastic shape memory struts 20 can self-expand in a radially disposed manner while simultaneously foreshortening along the overall longitudinal axis A of the anchor device 10. The anchor device 10 can radially expand within the subcortical cancellous bone to a dimension or dimensions that exceed the dimension of the generally round cortical defect through which the anchor device 10 was introduced. In the unexpanded state, the anchor devices described herein can be between about 3 mm-8 mm in diameter and can be between about 10 mm-30 mm in length. In some implementations, the anchor device is approximately 6 mm in diameter and 20 mm in length. It should be appreciated that the anchor devices described herein can be deployed using passive or active deployment or a combination of the two. For example, the anchor devices described herein can undergo initial passive deployment for provisional fixation in the bone channel and then active tensioning for full and final expansion.

Figure 2:
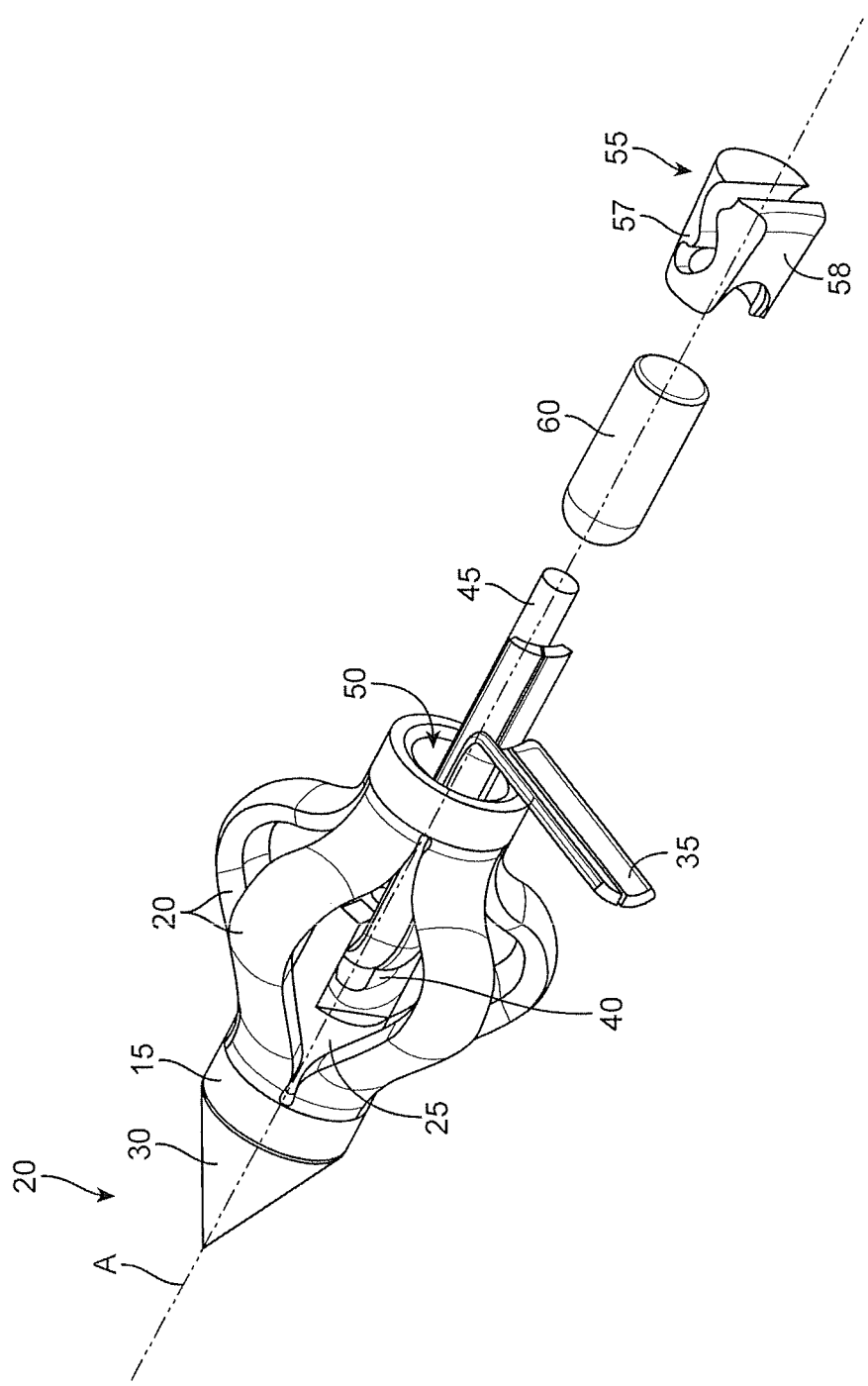
FIG. 2 shows a perspective, exploded view of the anchor device of FIG. 1 in an expanded state.

As shown in FIG. 2, suture strands 35 can be affixed to body tissue (primarily soft tissue, such as ligament, tendon, or joint capsule) and advanced through the proximal aspect of the distal wall slot 814 of the constraining element 810 of the deployment tool 800 and through the proximal aperture 50 of the device's tubular body 15 prior to placing the anchor device 10 within the bone. The suture strands 35 can be advanced distally along the longitudinal axis A of the anchor device 10 to a distal suture attachment feature 40 of the device. The attachment feature 40 can be a pulley, cleat or other element having similar configuration and/or function to progressively tension the sutures and approximate the attached soft tissue element to the proximal aspect of the device. The attachment feature 40 can facilitate the redirection of the suture material 35 providing for the suture ends to be delivered again along the longitudinal axis A back towards a proximal end of the anchor device 10 and back out through the proximal aperture 50 and, in some implementations, into a handle mechanism of the deployment tool 800.

Figure 5:
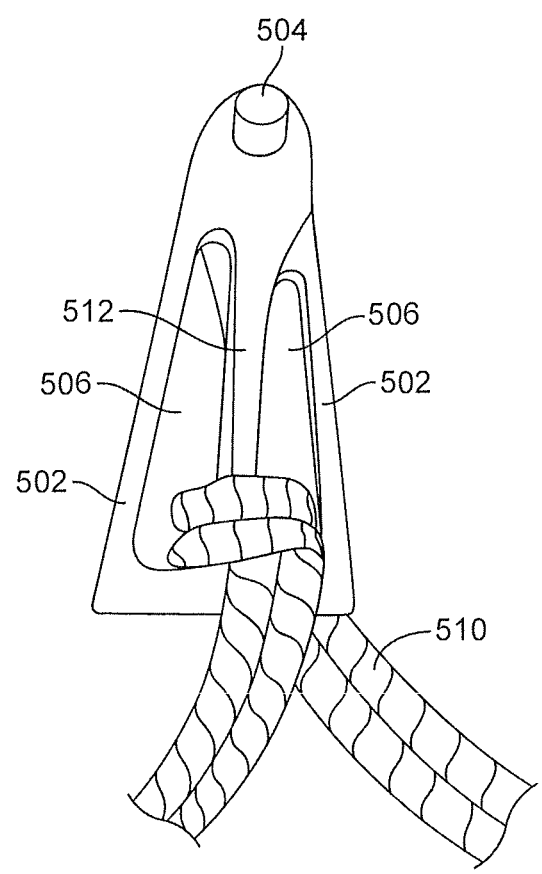
FIG. 5 shows a perspective view of an implementation of a cleat element for tensioning sutures to the anchor device of FIG. 1.
Figure 6:
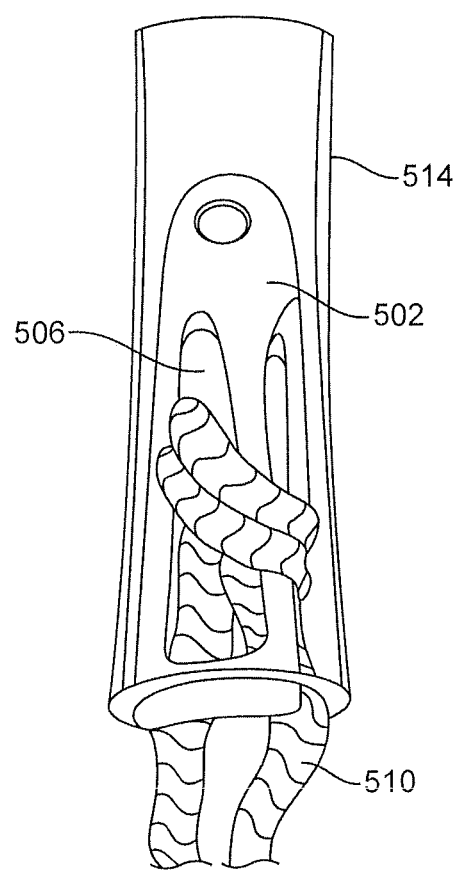
FIG. 6 shows a perspective view of the cleat element in FIG. 5 held in a compact configuration with an associated suture in a confining element.

Other configurations of the attachment feature 40 are considered herein, such as those described in FIGS. 5 and 6. For example, FIG. 5 shows an interrelated implementation of an attachment feature 500 that can be used to progressively tension and lock suture to the anchor device 10. The attachment feature 500 can include a pair of suture anchoring elements 502 coupled together, for example by a pin 504, forming a collapsible cleat device. The pin 504 can couple the pair of suture anchor elements 502 together such that they can be tethered or hinged or articulate relative to one another between a generally aligned position to a generally splayed configuration. The pin 504 can be associated with a distal aspect of the anchor device 10, for example attached to or integrated with the body of the anchor device 10, such that the attachment feature 500 is otherwise affixed to the anchor device 10.

Additionally, each of the suture anchor elements 502 can include at least one aperture 506 that can allow suture 510 or a pliable suture passing component, to pass through. This can allow for a variety of methods of securing suture 510 to the suture anchor elements 502 and the anchor device 10. For example, the suture 510 can be fixed to the attachment feature 500 by passing at least a part of the suture 510 through the proximal aperture 50 of the anchor device 10 and into the interior cavity (including following deployment of the device). In addition, at least a part of the suture 510 can be routed through the aperture 506 of at least one of each of the suture anchor elements 502 (see FIG. 5). The suture 510 can be routed in such a manner as to position a part of the trailing portion of the suture (i.e. those parts of the suture 510 closer to the soft tissue that is being approximated and anchored to the bone), underneath a portion of the leading portion of the suture (i.e. the portion of the suture that is closer to the end of the suture that is being pulled in tension), such that the tensioned suture will resist loosening due to friction resulting from one portion of the suture compressing another portion of the same suture. This effectively results in a unidirectional tensioning or cleating effect.

The devices described herein can be self-expanding and include a pre-deployment confined configuration. In some implementations, the confined or constrained configuration can be at least in part maintained by a circumferential ring or tubular element. While the suture anchor device is in a deployed state, the circumferential ring element can provide a suture abrasion protective function resulting from one or more of a variety of surface features and deployment positions (i.e., located between the suture material and the bone).

The suture 510 routed through the proximal aperture 50 of the anchor device 10 (as seen in FIG. 1), and then through the attachment feature 500 apertures 506 of one or both suture anchor elements 502 (seen in FIG. 5), can also include at least one circumferential wrap around a common post 512 of the distal suture attachment feature 500. The common post 512 can include adjacent or opposing post elements from each of the suture anchor elements 502. Once the suture 510 has been wrapped around the common post 512, the suture 510 can be routed back out of the proximal aperture 50 of the device 10. The routing of suture material in such a manner as to have the trailing portions of the suture material (i.e., the part of the suture material that is closest to or attached to the soft tissue) overlap those portions of the suture material that are being actively tensioned (i.e., the part of the suture material that has been routed back through the proximal aperture) can assist in creating a cleat-like unidirectional tensioning of the suture. The cleat mechanism can allow tensioning of the suture 510 while preventing subsequent loosening of tension placed on the suture 510 associated with the suture anchor elements 502 and the soft tissue to which the suture 510 is attached.

Figure 7A:
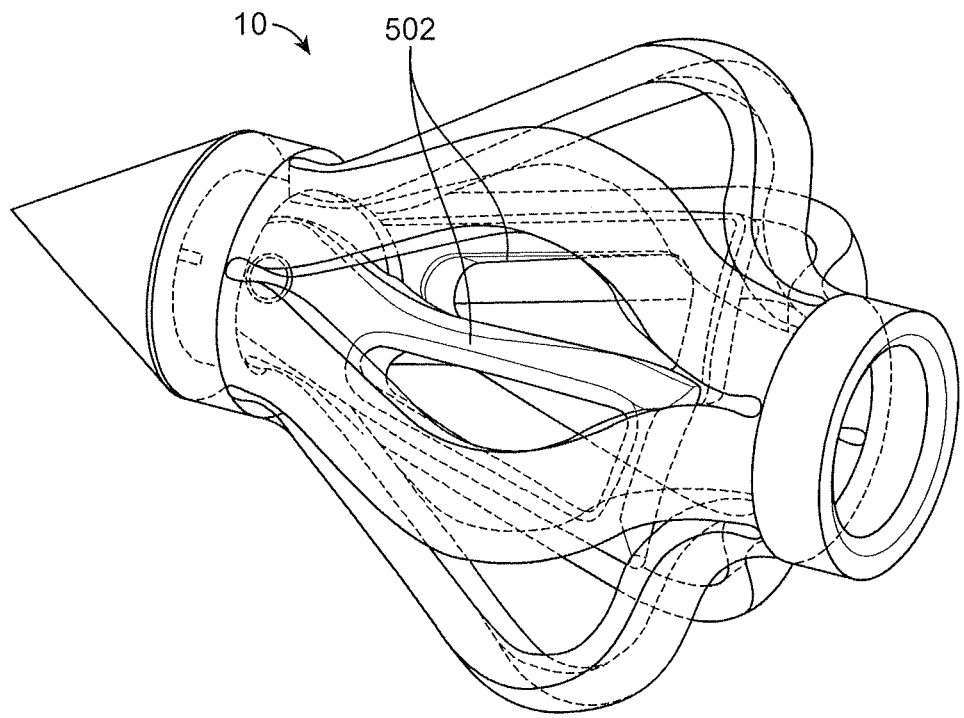
FIG. 7A shows an implementation of an anchor device in an expanded state and including a cleat element.

FIG. 7A shows an interrelated implementation of the anchor device 10 in an expanded configuration and having a pair of suture anchor elements 502 (suture not shown). As described above, the suture anchor elements 502 can provide tensioning of suture, such as unidirectional suture tensioning, which can assist in securing the positioning of tissue within a patient's body.

Figure 7B:
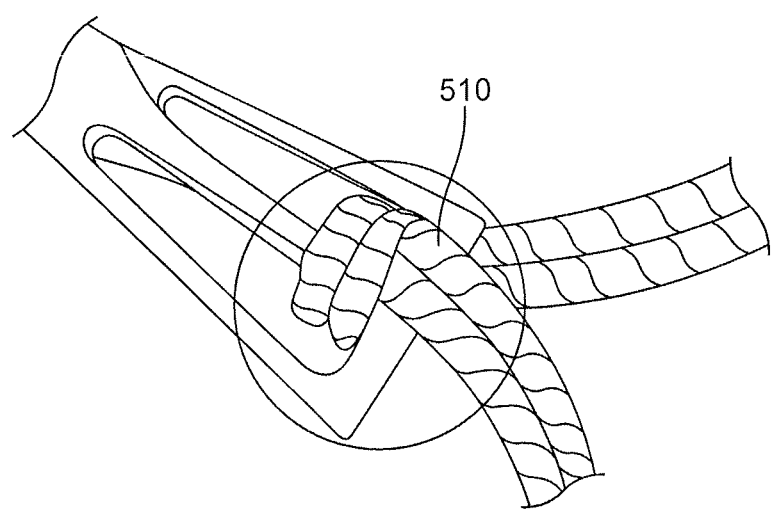
FIG. 7B shows an example suture pattern or formation for unidirectional suture tensioning.

FIG. 7B shows an example suture pattern or formation for unidirectional suture tensioning. In addition, the unidirectional suture tensioning formation can be formed using the suture anchor elements for tensioning suture and positioning tissue associated with the suture.

Figure 8:
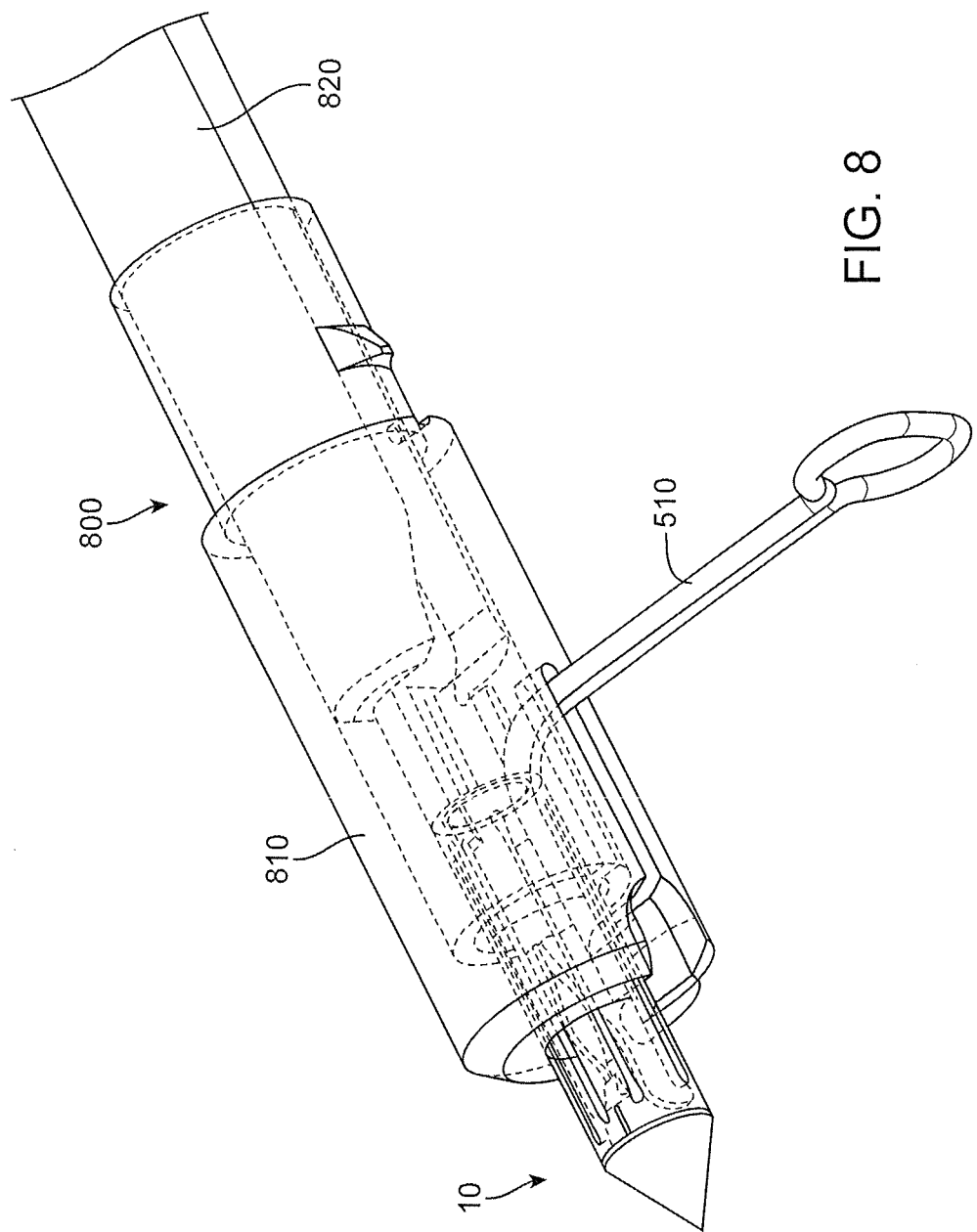
FIG. 8 illustrates an implementation of an anchor device coupled to an implementation of an implant deployment tool in a constrained configuration.

FIG. 8 illustrates an implementation of an anchor device 10 coupled to an implant deployment tool 800 in the constrained configuration. The implant deployment tool 800 can include a variety of features for assisting in positioning and deploying the anchor device 10, as well as for manipulating (i.e., cutting, tensioning, positioning, etc.) suture associated with the anchor device 10. As shown in FIG. 8, the implant deployment tool 800 can include a constraining element 810 which can assist in restraining the anchor device and preventing the anchor device 10 from expanding, at least until desired. In addition, the implant deployment tool 800 can include an advancing element 820 which can assist with advancing and deploying the anchor device 10, as well as cutting the suture in order to remove excess suture.

Figure 9:
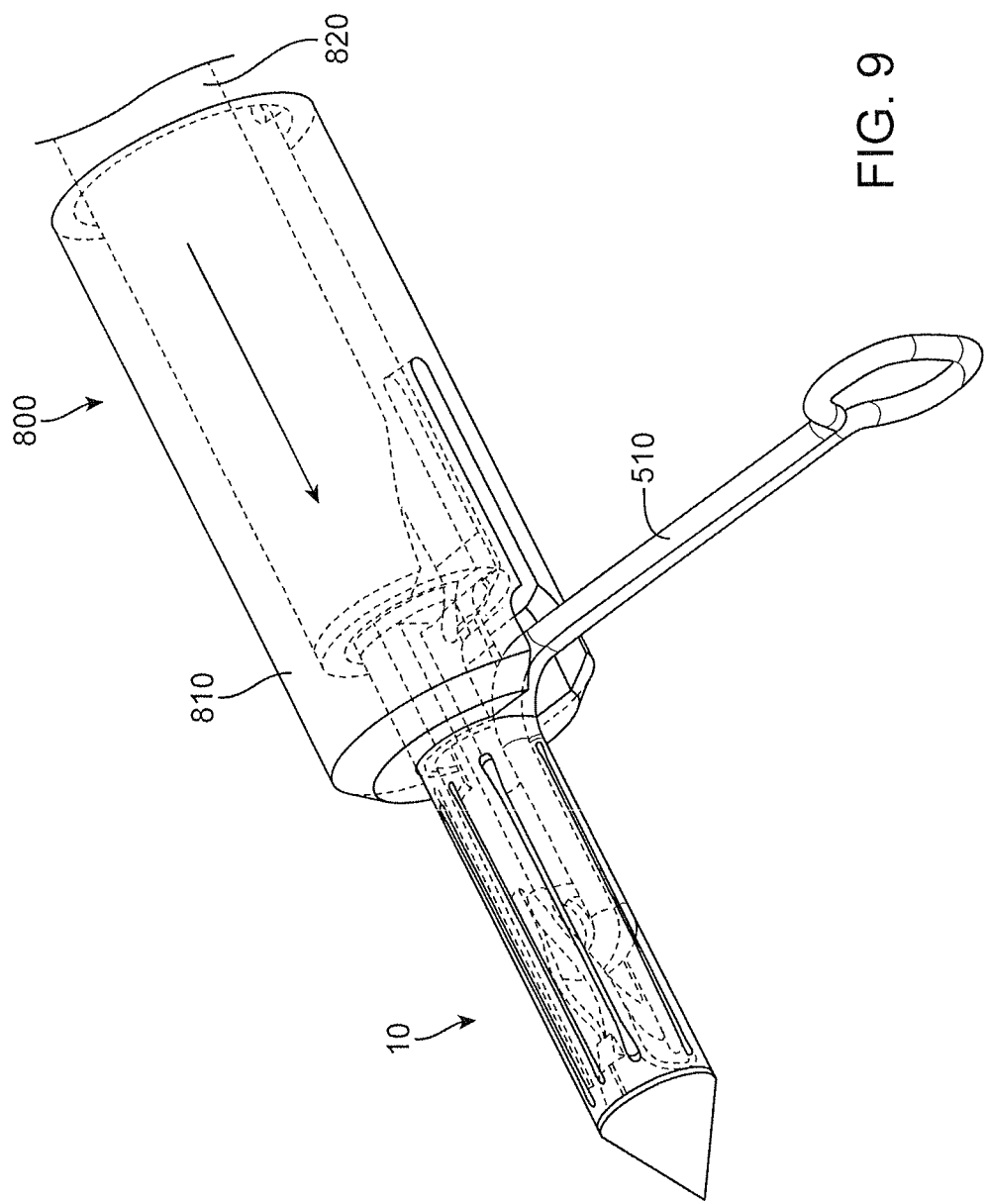
FIG. 9 illustrates the anchor device of FIG. 8 advanced along a part of the implant deployment tool and in an unconstrained configuration freeing the anchor device to expand and become secured to bone material.
Figure 10:
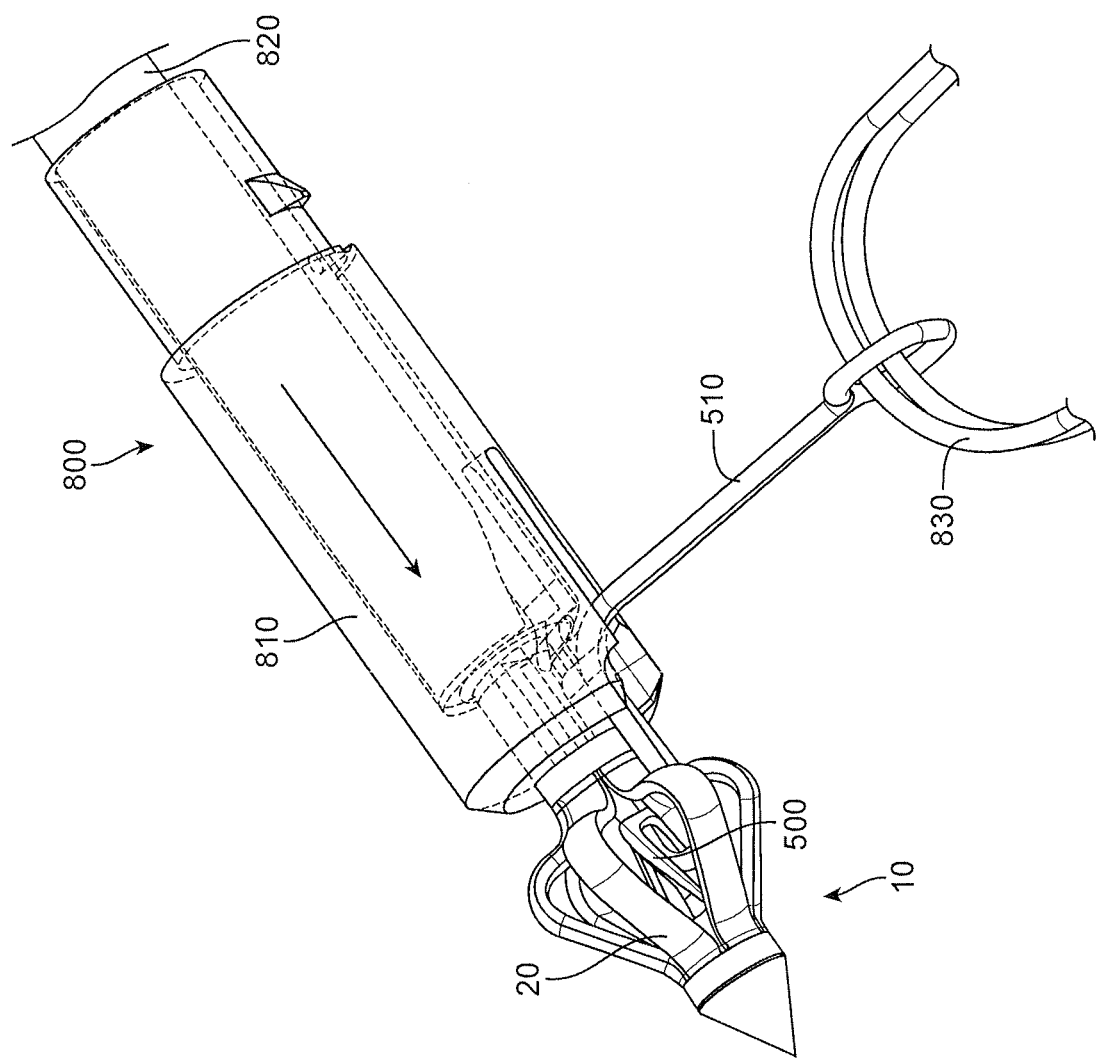
FIG. 10 illustrates the anchor device of FIG. 9 in an expanded configuration with suture extending from the anchor device and secured by a suture loop to soft tissue.

As shown in FIGS. 8, 9, and 10, suture 510 can be secured within the anchor device 10, such as secured to the suture anchor elements 502 as described above, and can extend from the anchor device 10 and implant deployment tool 800 in order to attach to tissue. The suture 510 can include a feature, such as a suture passing loop 830, for routing suture attached to soft tissue 835 as shown in FIG. 10. The advancing element 820 of the implant deployment tool 800 can be advanced or moved in order to allow the anchor device 10 to deploy (such as from the constraining element 810) and expand, as shown in FIG. 10, which can allow the anchor device 10 to become securely implanted in bone material and assist with securing tissue associated with the suture 510.

The attachment feature 500 of the device, can be surrounded by the slotted tubular body 514 (see FIG. 6) having the plurality of struts in a confined state prior to deployment (see FIGS. 6 and 8) and expansion (see FIG. 10). Prior to deployment, the struts 20 of the device 10 can be contained or confined within a rigid, generally or nearly circumferential element, such as the constraining element 810, which can maintain the suture anchor elements 502 in a fully overlapped position (as shown in FIG. 6). The confining element, such as the constraining element 810, as well as the tubular body 514 can allow the attachment feature 500, including the pair of suture anchor elements 502, to be initially implanted and positioned in a confined configuration, such as in an overlapped configuration forming a reduced combined width while still accommodating the positioning of suture or suture passing material through the apertures 506. In addition, the constraining element 810 can allow the suture anchor elements 502 to hinge into an expanded position, such as pivoting relative to one another, upon removal or decoupling of the constraining element 810 allowing the struts 20 to expand, as shown in FIGS. 2 and 7A. Once the constraining element 810 has been removed or decoupled from the attachment feature 500, including the suture anchor elements 502, at least the attachment feature 500 can expand. The suture 510 that is looped through the apertures 506 of the suture anchor elements 502 and around the common post 512 can then be pulled in tension, which can cause the splaying of the suture anchor elements 502 within the expanded anchor device 10.

In addition, a loop on the suture 510 can be used to pull suture material or cable 830 that has been previously associated with soft tissue (e.g. tendon or rotator cuff), through the suture anchor device along its routed path in the deployed or expanded position of the implant. The soft tissue structure can be pulled through the suture anchor device once the anchor has been inserted into the bone and deployed into an unconstrained configuration (as shown in FIG. 10). In addition, further tensioning of the suture 510 can approximate the soft tissue to which the suture 510 or suture material, such as a suture loop as illustrated in FIG. 10, is attached or associated with and hold the approximated soft tissue near or adjacent to the anchor device 10. Additionally, the cleat mechanism formed by the suture 510 and the suture anchor elements 502, acting effectively as a cleat, can assist in maintaining the suture in tension.

Figure 3:
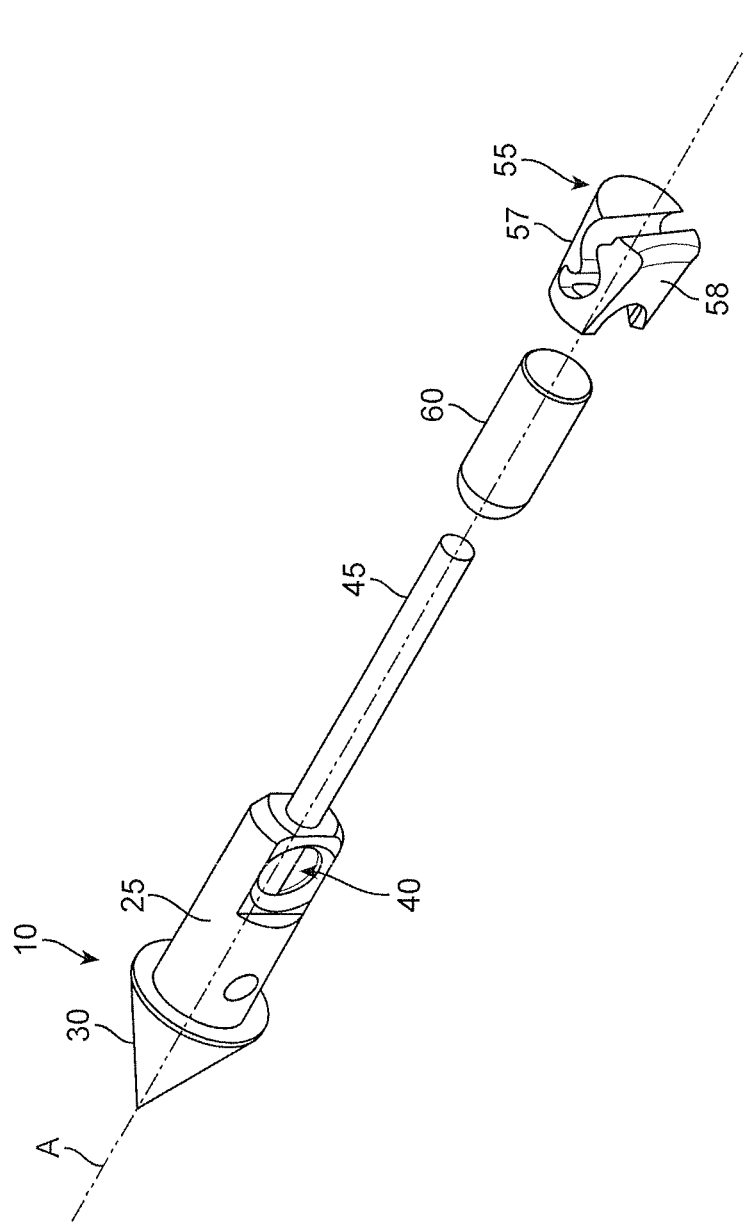
FIG. 3 shows a perspective, exploded partial view of the anchor device of FIG. 1 without struts.

As shown in FIG. 3, the anchor device 10 can also include a tensioning element 45. The tensioning element 45 can function similar or identical to the suture loop 510, as shown in FIG. 10. The tensioning element 45 can be routed around a distal pulley or post from a fixed location, such as an attachment element at the distal end region of the anchor device 10, such as near the distal end region of the inner body 25 or the tubular body 15 of the anchor device 10, and returning proximally through the interior volume along the central longitudinal axis A of the anchor device 10 and through the proximal aperture 50 of the tubular body 15 of the anchor device 10. The central tensioning element 45 can be a cable or suture material, such as ultrahigh molecular weight polypropylene fiber cable, Dacron fiber cable, or a combination of synthetic implantable fibers. The tensioning element 45 can approximate the distal and proximal ends of the anchor device 10 as well as approximate the soft tissue to the bone within which the implant was deployed. The central tensioning element 45 can extend into a handle mechanism of the deployment tool. The proximal aspect of the central tensioning element 45 can extend within the deployment tool to a tensioning mechanism. Such a tensioning mechanism can include an active ratcheting element or passive spring, which when deployed can provide loading of the tensioning element 45, foreshortening of the anchor device 10 as the proximal end region and the distal end region are brought towards each other as radial expansion of the device's perimeter struts 20 occurs. It should be appreciated that the device 10 can be self-expanding, manually expanding, as well as a combination of self-expanding and manually expanding. For example, the anchor device can self-expand to a degree upon release of a constraint on the struts 20 and then manually expanded using tensioning mechanism such as the tensioning element 45 to cinch the ends toward one another to achieve a fully expanded maximal diameter.

With the perimeter struts 20 fully deployed (see FIG. 2), a mechanism within the deployment tool 800 can provide for tensioning of the suture strands 35 and approximation of tissue, such as soft tissue like a tendon, to which the suture strands 35 are affixed toward the proximal aperture 50 of the implant's tubular body 15. Once sufficient tensioning of the suture strands 35 has been deemed to have occurred, a peripherally hinged crimping element 55 can be advanced distally from the deployment tool along the longitudinal axis A of the anchor device 10 confining and ultimately trapping the suture strands 35 near and/or within the proximal aperture 50 of the tubular element 15. In some implementations, the crimping element 55 can have a generally conical external geometry, initially hinged open to accommodate the tensioning of the central tensioning element 45 and the suture strands 35, prior to crimping. In addition, as the crimping element 55 can be urged within the proximal aperture 50 of the tubular element 15, the interaction of the internal bore of the tubular element 15 with the external geometry of the crimping element 55 can result in the crimping element 55 hinging closed to trap and fix the tension of the suture stands 35.

In some implementations, the opposing internal surface features 57, 58 of the crimping element 55 can interdigitate with closure, providing for optimized friction lock of the suture strands 35 and central tensioning element 45 within. The surface features 57, 58 can additionally include opposing sharp proximal edges that either meet or overlap in a scissoring manner, resulting in division of the suture strands 35 and central tensioning element 45 at a tip of the crimping element 55 and most proximal aspect of the tubular body 15. The internal bore of the proximal aspect of the tubular body 15 of the anchor device 10 can have a conical geometry that can match the geometry of the external surface of the crimping element 55 in the crimped configuration. The crimping element 55 can also include a side slot for capturing the suture strands 35 within the crimping element 55 from the side.

In an implementation of deployment, a suture strand(s) 35 can be placed through a tissue or other material that is intended to be approximated to bone. The "free" suture ends 35 can be passed by way of suture passers (such as by wire cable or synthetic cable coursing along the intended course of the sutures within the device) that are pulled or tensioned along with the attached free ends of the suture 35 within the device deployment tool. With the sutures 35 secured to the device deployment tool 800, the pointed tip 30 of the anchor device 10, which can extend distally beyond the distal end of the constraining element, can be delivered along a soft tissue path that minimizes the potential for a soft tissue bridge (i.e. superficial soft tissue that is trapped between the tensioned suture strands and the bone). This can be accomplished with a variety of strategies, such as using an introductory cannula or by placing tension of the sutures 35 with one of the surgeon's hands and then sliding the delivery shaft and anchor device 10 immediately adjacent and along the axis of the tensioned suture strands 35 with the other hand.

Once the anchor device 10 is delivered into close proximity to the bone's cortical surface to which the suture strands 35 are intended to be approximated, the sharp distal tip 30; which might include a trocar geometry and/or very sharp tip, can be tapped through the cortex or pushed through a pre-drilled hole. The anchor device 10 and device deployment tool 800 can be advanced until the distal edge 818 of a constraining element 810, which can have a larger diameter than the cortical defect or channel through which the distal tip 30 has been advanced, is positioned up against the outer cortex of the bone (see, for example, FIG. 4C). The constraining element, such as the constraining element 810 shown in FIG. 4C or FIG. 8, can thus serve as a shoulder stop and stabilizing feature for the device deployment tool. A tubular deployment element, such as the advancing element 820 shown in FIGS. 4C and 8, can be advanced within the internal bore 812 of the constraining element 810, pushing on the proximal surface edge of the tubular outer body 15 of the anchor device 10, advancing the anchor device 10 within the bone such that the proximal edge of the proximal aperture 50 is generally located at or near the external cortical surface of the bone. This deployment can be accomplished by a push-pull mechanism or relative linear translation of the advancing element 820 relative to the constraining element 810 with reactive forces transmitted to the cortical surface of the bone by the shoulder restraining feature of the distal edge 818 of the constraining element 810. This can reduce the risk of unintended fracture or cracking of the cortical bone adjacent to the introductory cortical bore. Further, this can avoid the need to restrain the deployment forces imparted by the deployment mechanism 800.

Once delivered within the subcortical location, the anchor device 10 may be radially expanded via a passive process mediated or effected by the shape memory properties of the superelastic metal alloy of the struts 20. This can be followed by active tensioning of the suture leads until the suture is optimally tensioned and the attached tissue is sufficiently approximated to the devices cortical entry location. Tensioning of the suture leads can be accomplished with a variety of mechanisms, including opposing cam configured cleats or a ratcheting reel mechanism. In an implementation, the tensioning of the suture 510 and radial expansion of the struts 20, is accomplished via the unidirectional tensioning feature of the dual aperture and common post cleat elements, such as described above in reference to FIG. 5.

A crimping element 55 (shown in FIGS. 2 and 3) can then be advanced over or onto the tensioned central tensioning element 45 and the tensioned suture strands 35, until they are restrained from subsequent displacement. The crimping element 55 can include an element within which the suture strands 35 can be trapped by progressive approximation of opposing walls within the proximal aperture 50 of the anchor device 10. According to another implementation for securing the sutures and tensioning element(s), a tapered interference pin 60 can be delivered within the proximal opening or aperture 50 of the anchor device 10. The pin 60 can have sufficient cross-sectional area and length to provide for an interference fit with the surrounding suture 35 and tensioning element(s) 45.

A cutting tool or cutting feature can be situated at the upper end of the crimping element 55 can be used subsequent to the crimping or trapping of the tensioned suture 35 and tensioning element(s) 45 to cut the cable elements of the suture and tensioning element(s). The device delivery mechanism can be separated due to suture and central tensioning amputation from the delivered, deployed device, and approximated tissue. In an implementation, the suture 510 may be cut via a rotating blade element within a deployment tool's shaft, which can also be in close proximity to the proximal aperture 50 of the anchor device 10.

FIGS. 4A-4I show interrelated implementations of an anchor device 400 and a deployment tool 800. The anchor device 400 can include a body 415 having a plurality of slots 417 forming a plurality of stays or struts 420 at least partially surrounding an interior volume 445 of the body 415 (see FIG. 4A). The anchor device 400 can include two or more longitudinally extending slots 417 along its long axis A from a distal end region 410 to a proximal end region 412 on its body 415 that can define the edges or margins of the deployable struts 420. The anchor device 400 can employ similar radially expanding features to secure the anchor device 400 with the medullary cavity of the bone as described above.

It should be appreciated that the anchor device 400 as well as any of the anchor devices described herein can be deployed using passive or active deployment or a combination of the two. In some implementations, the plurality of struts 420 passively transition from a constrained, delivery configuration that is radially contracted and axially elongated to a relaxed, deployment configuration that is radially expanded and axially shortened. The anchor device 400 can include a self-expanding super-elastic shape set material, such as nitinol, that prior to deployment is maintain in a constrained configuration having a reduced diameter along a segment of its length that passively radially expands with deployment within the internal confines or medullary cavity of the bone. The anchor device 400 can rely solely upon the properties of the shape memory, super-elastic material (e.g. nitinol) to spontaneously revert (once unconfined) to a radially enlarged configuration with deployment. The anchor device 400 described herein can undergo initial passive deployment for provisional fixation in the bone channel and then active tensioning for full and final expansion. The passively deployed expansion can be purely within the subcortical region of the bone.

In some implementations, the anchor device 400 can be configured to anchor soft tissues 405 (see FIG. 4C) such as tendon or other tissue to or within a rigid material such as bone 401. The anchor device 400 can be used to deliver and secure a generally cylindrical segment of a detached tendon's terminus within a closely confining bore or channel 404 of bone 401. Examples of detached tendon can include, the origin of the proximal long head of the biceps, the insertion of the biceps tendon in the proximal radius, extensor carpi radialis, the infrapatellar tendon of the quadriceps muscle, the anterior tibialis, the Achilles tendon, and extensor tendons of the digits. These tendons are generally detached from bone that has a dense cortical shell and a relatively soft medullary cavity. It should be appreciated, however, that the anchor device can be used to anchor other tissues and/or materials to bone as well.

The anchor device 400 can position the soft tissue 405, such as a tendon to be affixed, within the interior volume 445 of the highly porous body (for example, by virtue of the plurality of slots 417 and struts 415) of the expanded device 400 while providing for intimate contact with the cortical cancellous bone 401. The tendon or soft tissue 405 to be affixed can be secured to the anchor device 400 via a cable or suture 403 that is weaved through the soft tissue 405 and then tied or otherwise secured to the distal end region 410 of the anchor device 400 (see FIG. 4D). Thus, the tendon or soft tissue 405 can be tensioned separately from deployment of the anchor device 400 into the expanded configuration. A suture weave provides a safer way to secure the soft tissue 405 that is less likely to strangulate or prevent blood from circulating through the section of soft tissue 405 being secured which can necrose the soft tissue. Further, cradling the soft tissue 405 to be affixed within the highly porous architecture of the device 400 approximates the soft tissue 405 to the bone 401 in a manner that limits the compression of the soft tissue 405 against the cortical rim and affords abundant opportunity for vascularization of the soft tissue 405 as well as fibrous and boney attachments to the perimeter of the soft tissue 405. Further, the passive deployment of the anchor devices described herein upon insertion into bone such that expansion within the subcortical region occurs is less surgically challenging.

Loads imparted by tendon tensioning can be high and as such sufficient wall thickness and deployed rigidity are desired to overcome loads imparted by tendon tensioning and to prevent the anchor device 400 from collapsing through the small cortical defect through which it is inserted. The anchor device 10 described above may have substantially thinner device walls compared to anchor device 400 to facilitate active expansion using the central tensioning element.

Figure 4A:
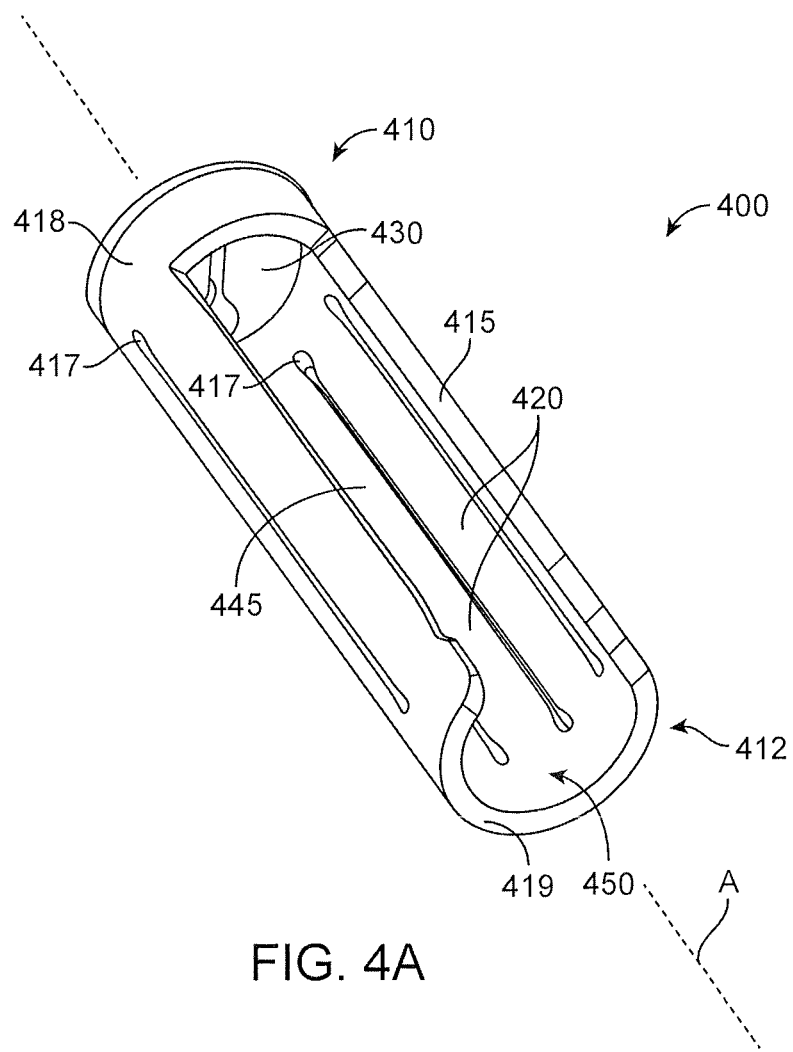
FIG. 4A shows a perspective view of an implementation of an anchor device in a constrained configuration.
Figure 4B:
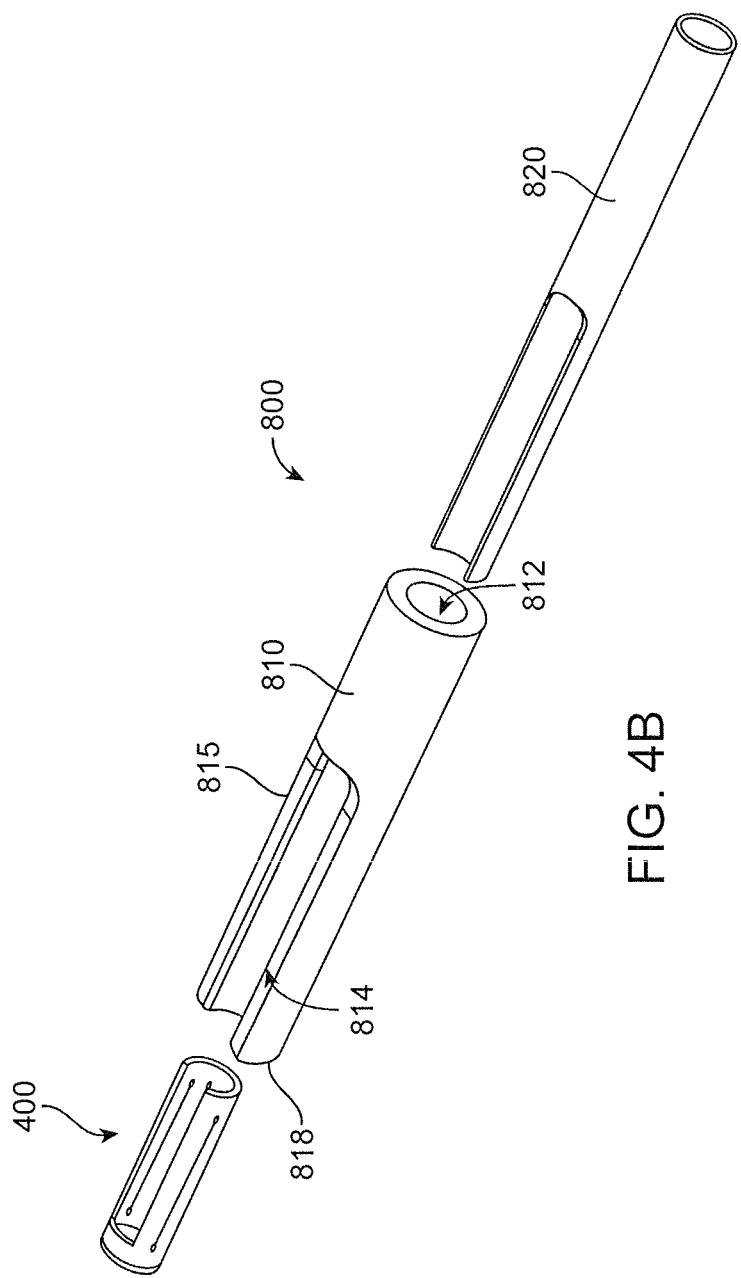
FIG. 4B shows a perspective view of the anchor device of FIG. 4A and an exploded view of an implementation of a deployment tool.
Figure 4C:
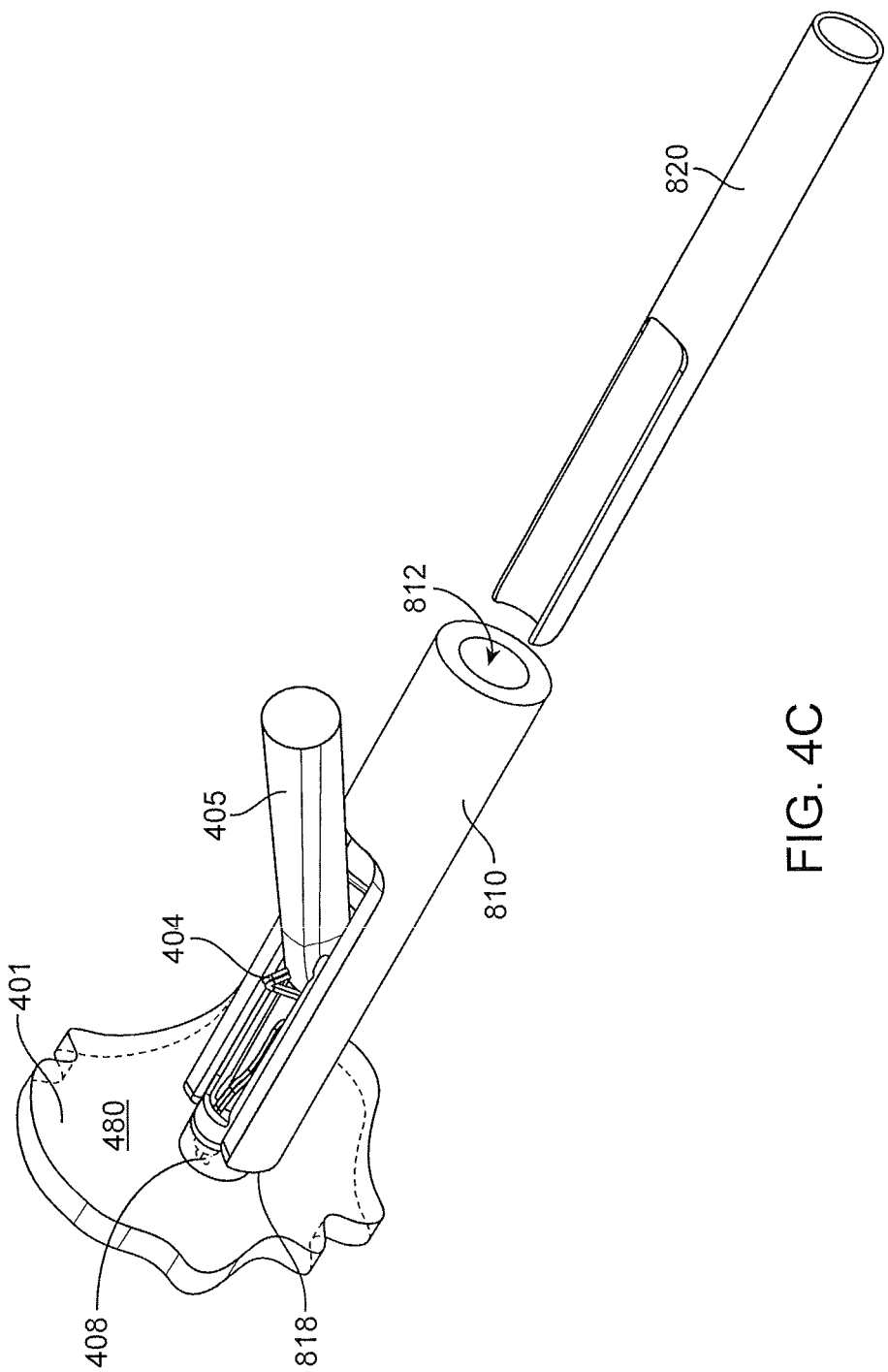
FIG. 4C shows a perspective view of the anchor device and deployment tool of FIG. 4B with an associated soft tissue and relative to a bone.
Figure 4D:
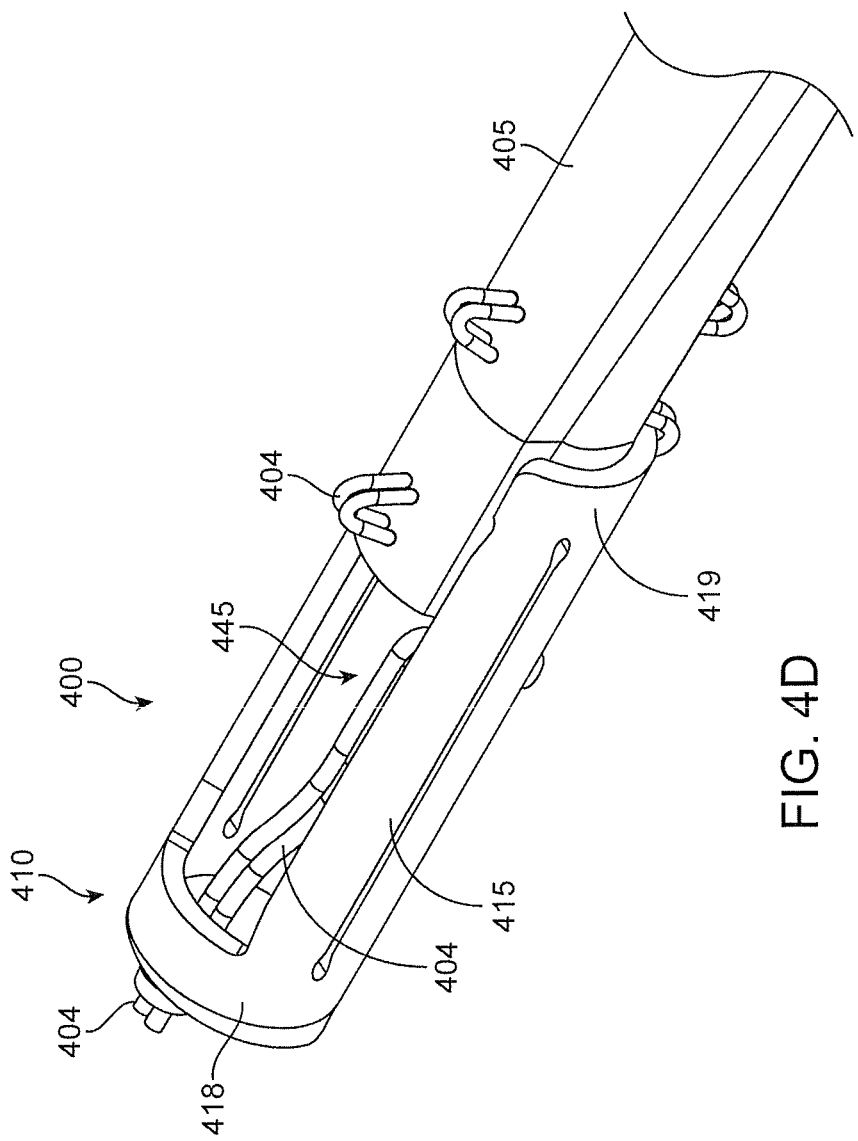
FIG. 4D shows a perspective view of the anchor device of FIG. 4A with an associated soft tissue.
Figure 4E:
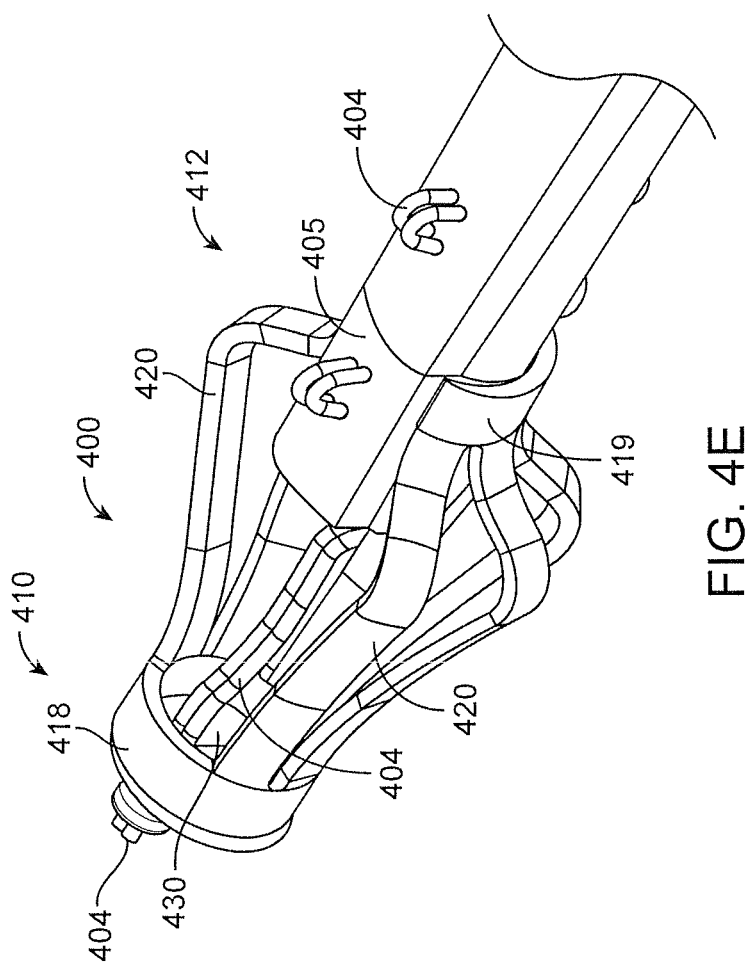
FIG. 4E shows a perspective view of the anchor device of FIG. 4D with an associated soft tissue and in an expanded state.

A soft tissue 405, such as a tendon terminus, can initially be positioned and secured, through the proximal aperture 450 and into the bore or internal volume 445 of the body 415 (see FIG. 4D). In its confined and reduced diameter state, the body 415 forms a substantially tubular or cylindrical shape and the struts 410 surround the internal volume of the body 415. The soft tissue 405 can be secured to the anchor device 400 such as by an attachment feature 430 positioned within the internal volume 445 of the body 415 near a distal end region 410. The soft tissue 405 can be attached, for example, by weaving, tying or crimping or otherwise passing suture material 404 through the detached soft tissue 405. In an implementation, the suture material 404 attached to the soft tissue 405 is tied to an attachment feature 430 positioned within the interior volume 445 of the body 415 near the distal end region 410 of the implant 400, either before or after the implant 400 has been delivered with the soft tissue 405, into the bone 401.

The attachment feature 430 can be positioned within the interior volume 445 of the body 415 for example near the distal end region 410 (e.g. the end of the anchor device 400 that is first introduced through the bone 401) and can be configured to secure the tissue 405 to be attached to the bone 401 to the anchor device 400. The attachment feature 430 can include a post, slot, pulley, cleat, crimping element or other element as described herein to facilitate securing or coupling of materials such as a suture material and/or a soft tissue 405 to the anchor device 400. In some implementations, the attachment feature 430 can include a saddle shaped element to which at least two suture ends 404 can be passed around and subsequently knotted or crimped to secure the tendon 405 associated with the suture 404 within and/or to the anchor device 400 (see FIG. 4F). In other implementations, the attachment feature 430 can be a post extending transverse to the long axis of the device (see FIG. 4I) near the distal end region 410.

Figure 4F:
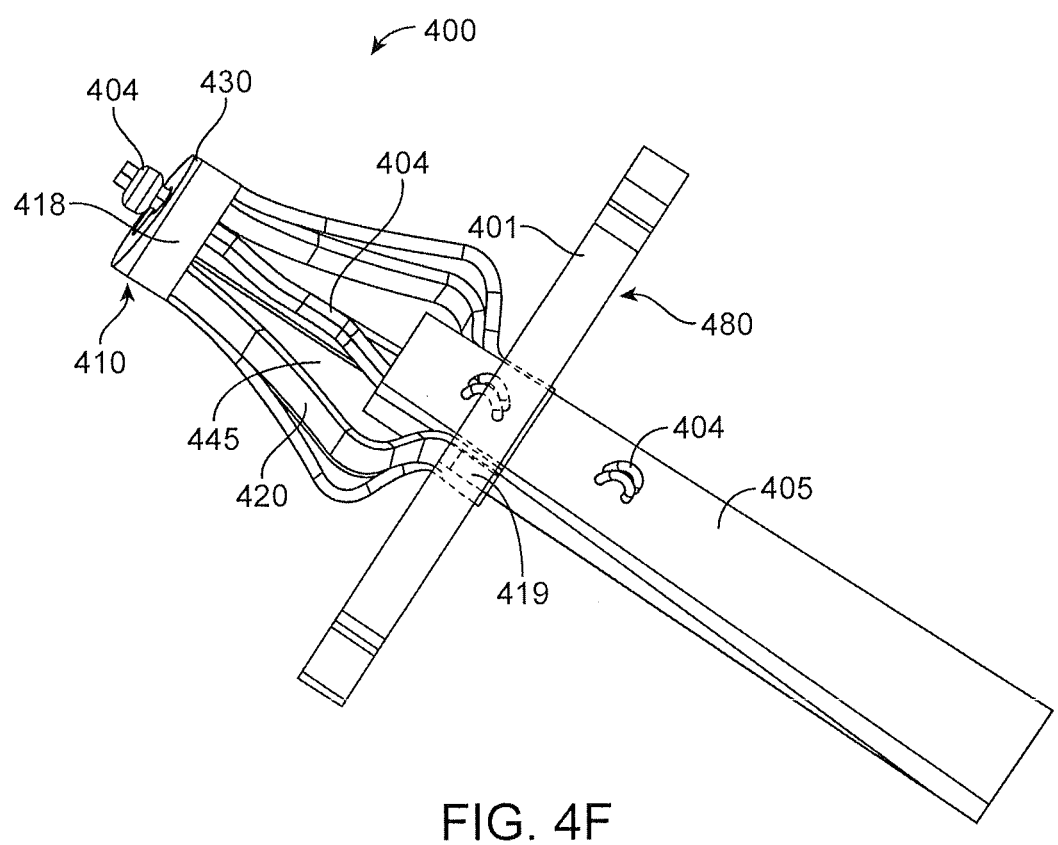
FIGS. 4F-4H show various views of the anchor device of FIG. 4E with an associated soft tissue in an expanded state and deployed within a bone channel.
Figure 4G:
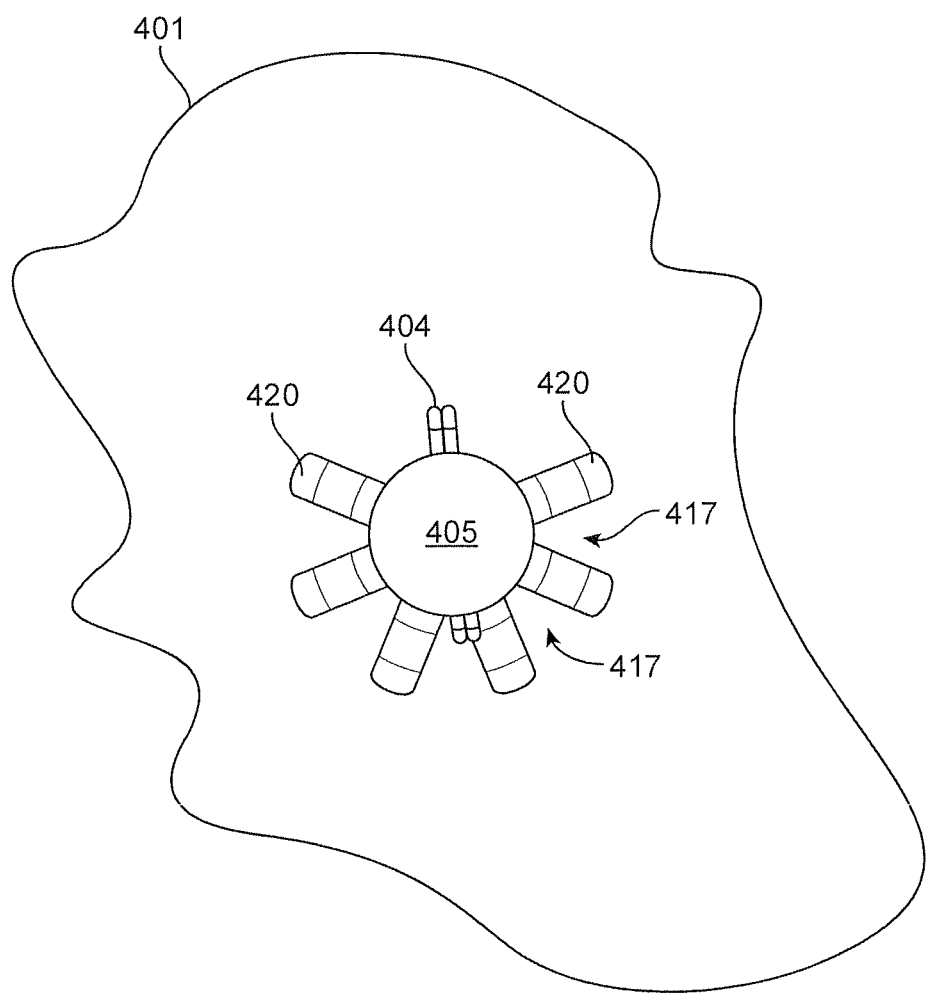
Figure 4H:
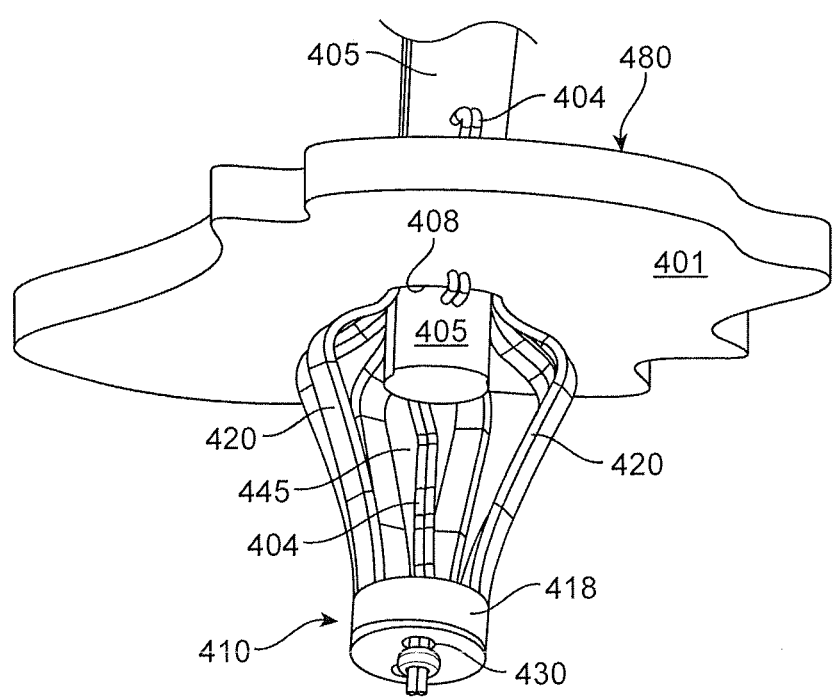
Figure 4I:
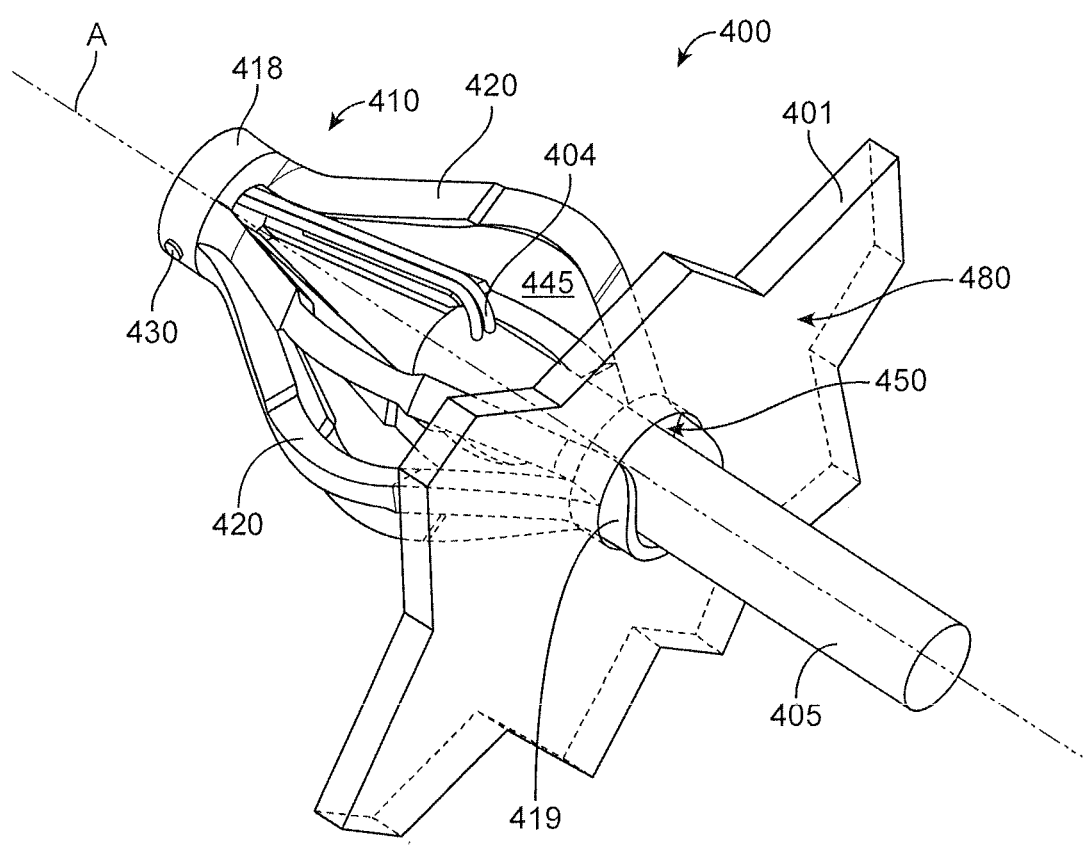
FIG. 4I shows another implementation of an anchor device with an associated soft tissue in an expanded state and deployed within a bone channel.

Once secured to the anchor device 400, the soft tissue 405 and the anchor device 400 can be delivered from the exterior surface 480 of the bone 401 through an appropriately sized and fashioned channel 408 or cortical defect (e.g. a drill hole sized to near the diameter of the tendon-device construct into the medullary cavity or internal canal of the bone 401) (see FIGS. 4C and 4F). A mechanical constraining element 810 of the deployment tool 800 can be positioned to surround at least a portion of the device 400 maintaining the struts 420 in a generally straight, reduced diameter configuration suitable for insertion through the channel 408. The constraining element 810 can be a relatively rigid tube or a ring-like structure. In some implementations, the constraining element 810 can be a tubular structure having an outer wall 815 surrounding an inner channel 812 and having a slot 814 extending through at least a portion of the outer wall 815 (see FIG. 4B). Separation of the constraining element 810 from the anchor device 400, permits the shape set super-elastic material of the anchor device 400 to spontaneously revert to its shape set deployed geometry having an enlarged diameter (see FIG. 4E). The enlarged diameter of the deployed configuration can be sufficiently larger than the bone channel 408 or cortical defect through which the anchor device 400 was introduced. This prevents and/or resists potential disengagement of the anchor device 400 and its attached soft tissue 405 from the bone 401, for example when placed under high loads during tendon tensioning and muscle contraction.

The struts 420 can be asymmetrically configured, such that when the device is deployed and the struts 420 expand radially from the long axis A of the anchor device 400, tensioning on the attached soft tissue 405 can result in off axis (i.e. tilting) displacement of the device, providing enhanced resistance to undesired displacement and "explantation" of the device and tendon from the bone's medullary cavity. In some implementations, the struts 417 can be shaped such that they have non-uniform wall thickness. For example, the struts 417 can be thinner near a central region and thicker near the distal and proximal ends. In other implementations, the struts 417 can have a reduced wall thickness where the struts couple to a ring-like structure that constrains the struts 417 and keeps the anchor device 400 in the reduced diameter configuration. The outer surface of the anchor device 400 can have a generally constant external diameter.

The anchor devices described herein, once implanted, can be put under a tensile load along the longitudinal axis A of the device. The tensile loads applied along the longitudinal axis A to the anchor device when in use can further approximate the distal end region to the proximal end region and result in further expansion of the struts away from the longitudinal axis A. Thus, the tensile load can act to further anchor the anchor device within the bone. In some implementations, suture or cable can be weaved through a detached tendon end that is being attached or repaired into the bone. The suture or cable can be tied or otherwise fixed to an attachment feature near or at the distal end of the device. As the tendon is placed in tension via muscle action or any other effect (e.g. elbow extension with the biceps tendon), the tension is transmitted to the distal end region of the device where the suture or cable material is attached. This tensile loading of the tendon and attached suture or cable maintains the anchor in the expanded configuration in which the distal end of the device is approximate to the proximal end of the device. The proximal end of the device is restrained in that the expanded struts are located immediately deep to the smaller diameter cortical defect. Thus, the device is kept compressed as a result against the deep surface of the cortical bone and the struts are in the deployed or expanded configuration.

The anchor devices described herein can also provide for limited contact with the surface features of the reattached soft tissue to optimize the biological repair process, for example, vascular and collagen repair within the bone to the tendon. In some implementations, the generally tubular geometry of the anchor devices described herein (at least in the constrained configuration) can be circumferentially disrupted along a segment of its proximal length while preserving circumferential continuity distally such that direct contact can occur between the soft tissues such as a tendon terminus and the adjacent tissues for optimal biological repair.

As best shown in FIG. 4A, the body 415 in its constrained configuration can be a generally cylindrical element having a plurality of slots 417 extending through the wall of the body 415 forming the plurality of struts 420. The plurality of slots 417 can be generally shorter in length than the overall length of the body 415 such that an outer wall 418 can be formed at the distal end region 410 of the body 415 and an outer wall 419 can be formed at the proximal end region 412 of the body 415. The outer wall 419 at the proximal end region 412 of the body 415 can form or define the proximal opening 450 into the internal volume 445 of the body 415. The outer wall 419 at the proximal end region 412 of the body 415 can be discontinuous forming a gap such that in cross-section it defines a generally c-shaped proximal opening 450 to the interior volume 445. Upon deployment of the anchor device 400, the discontinuous proximal outer wall 419 can be positioned near or within the bone channel 408 through which the anchor device 400 was delivered (see FIGS. 4E-4F). The gap or circumferential discontinuity in the proximal outer wall 419 of the otherwise cylindrical shape of the body 415 allows for at least a portion of the soft tissue 405 being delivered to be placed in direct intimate contact with the channel 408 or cortical defect in the bone 401 and medullary cavity of the bone, particularly the closely sized cortical defect, promoting tendon to bone healing. The gap in the proximal outer wall 419 can also provide for easier introduction of the tendon terminus 405 within the cavity or channel of the device and allow for asymmetric deployment/expansion of the device. Having the tendon or soft tissue 405 exposed along the circumference of the tendon-device construct and sizing the cortical defect 408 (e.g. drill hole) to provide for an intimate fit, can enhance not only the initial fixation but can also improve long term tendon biological fixation.

The devices described herein can be sterile packaged and confined in a delivery tube, with or without suture passers that can be employed to facilitate delivery of the suture strands (securely attached during surgery to the tendon) through the channel or aperture of the device and around the distal terminal post or saddle. A slot in the confining tubes distal end can accommodate the introduction of the tendon terminus. A small ring or grommet can be employed to maintain hoop strength of the confining delivery tube and serve to reduce abrasion after implantation of the tendon against a sharp external cortical edge.

A sizing guide can be used to determine the optimized size for the cortical defect (e.g. drill hole) needed to provide for intimate contact of the exposed tendon's surface with the cortical margin. The defect can be slightly undersized relative to the cross-section or diameter of the tendon-device construct, such that with introduction, the compliance of the tendon can provide for annular constriction of the tendon within the cortical defect. This can be facilitated by tightly winding an implantable low friction monofilament suture material around the delivery tube and tendon secured to the device prior to delivery. The low friction monofilament material can temporarily constrict and confine the tendon to a reduced cross-sectional geometry and with deployment introduction remain superficial to the bone (allowing for its removal) allowing the tendon to relax back into a geometry of larger cross-sectional area within the medullary cavity.

In another implementation of deployment, a constraining tube element with or without a disruption of the circumferential continuity of the constraining element can be further surrounded by a secondary confinement element to reinforce the inner constraining tubing element in its ability to constrain the self-expanding device in its reduced diameter, constrained geometry. The constraining element can have a disruption of the circumferential continuity, as in a distal longitudinal slot feature (e.g. to accommodate suture introduction and delivery to the confined device), or a thin walled constraining tube that alone and at room temperature would be insufficient to constrain the outward expanding forces of the constrained self-expanding device. A secondary constraining ring or tube can be maintained around the inner constraining tubular element to reinforce the constraining effect. The distal tip of the device can be chilled prior to removing the secondary external ring or tube, immediately or shortly prior to deploying the self-expanding device.

The outward displacing forces of the shape set material within a thin walled and/or slotted tubing may exceed the circumferential restraining strength of the constraining tubing (i.e. hoop strain resulting in deformation of the tubing or splaying). An alternative accommodation can be to provide sufficient restraint at room temperature storage of inventory or above to avoid thicker walled tubing confinement. The concept relies upon the two different material states of the differing material properties of the superelastic metal in the martensitic state and the austenitic state, as well as the properties within the transformational temperature range (i.e. from A s [Austenitic start] temperature to A f [Austenitic finish] temperature) for the expandable material composition of the device. In the Martensitic state, nitinol is relatively pliable and it is not superelastic. While in the Martensitic state at lower temperatures, it has a relatively low modulus of elasticity (compliant), while in the fully austenitic state it is superelastic and it has a relatively high modulus of elasticity (stiff).

It is proposed the relatively thin walled and/or slotted constraining tubes that house the superelastic self-expanding shape set device can be additionally constrained by an encircling larger diameter tubing (plus or minus circumferential in configuration, but in a preferred embodiment, circumferential), during inventory storage and transport of the device. Immediately prior or just prior to surgical application (e.g. within the preceding day, hours, or minutes) the device and in particular the components of the shape set superelastic material can be brought to a reduced temperature (relative to ambient) to condition the material in the transformation temperature range (e.g. refrigerated or immersed in a chilled or ice bath). With the material in the transformation zone temperature range, the most outer constraining tubular element can be removed, providing for adequate constraint from the thin walled and/or slotted tubing due to the reduced outwardly expanding force exerted by the chilled shape set and only partially superelastic material. For commonly used nitinol material this can be in the temperature range from −4 degrees Fahrenheit to 50 degrees Fahrenheit.

In addition it is contemplated the constraining elements either or both might have thermally insulating material disposed about their surfaces or as a coating to retard the warming effects of exposure of the chilled implant/delivery device once the most exterior constraining element has been removed. Once delivered, the implant can be warmed by local body heat or heated by various means (e.g. irrigation with warmed physiologic solutions) to facilitate transformation into the shape set superelastic state. The most external constraining element or tube can be associated with the device only during storage and can be removed or pulled off the distal tip of the device after bringing the devices shape set material to a lower than ambient temperature with various chilling means (e.g. refrigeration or chilling bath) while in the immediate operative setting or immediately prior to surgery. This can allow for the use of a thinner walled and/or slotted constraining tube immediately surrounding the nitinol during surgical delivery. An implementation of the previously described variant includes the use of a physiologic solution to warm the deployed device to promote expansion in situ.

The plurality of struts of the devices described herein can provide the body with a defining perimeter having various shapes. The shape of the expanded anchor device can vary depending on the region in which the anchor device is expanded. Generally, the plurality of struts expand outward from the longitudinal axis A of the device such that they take on a curved, or otherwise bowed shape. The plurality of struts can bow radially outward from a central axis A of the anchor device such that the perimeter of the expanded anchor is generally conical in shape. Each of the struts can expand to a greater extent near the proximal end region of the device compared to the distal end region of the device (see, for example, FIG. 7A). The amount of expansion and extension of the struts away from the longitudinal axis A near the proximal end region of the anchor device aid to resist pull-out of the anchor device from the bone. The plurality of struts also can expand outward such that a portion of the struts is bent to a certain angle giving the device a more angular perimeter shape. The plurality of struts can provide the device with a variety of perimeter shapes including fusiform, oblong, spheroid, umbrella, oval, wedge, cone, frustoconical, pyramidal, triangular, half-moon, or other shape that can be symmetrical or asymmetrical. It should be appreciated that the plurality of struts in the devices described herein can be disposed symmetrically or asymmetrically around a central axis of the device.

As described herein, the surface geometry of the anchor devices can be generally discontinuous such that a plurality of slots define the plurality of struts. The width of the plurality of slots can vary resulting in variable widths of each of the plurality of struts. Further, the number of the slots and thus, the number struts can vary. The struts can be made thicker or thinner to achieve a particular strength for a particular purpose. Further, the thickness of each of the struts can vary along their length such that a portion near a distal end region or a proximal end region is thicker than a centrally disposed portion of the strut. Each of the struts can have a wider, more flattened configuration or can have a more rounded wire-like configuration. The wall thickness and width of the struts can be uniform or non-uniform.

The anchor devices described herein can be constructed of one or more biocompatible materials. In some implementations, one or more portions of the anchor devices, such as the struts, are formed of a biocompatible memory-shaped alloy (e.g. Nitinol, titanium/nickel alloy, nitinol wire mesh) with or without radiolucent material (e.g. PEEK®, Victrex Corp., PolyEtherEtherKetone, or other polymer material). Use of both radiodense and radiolucent elements within the devices provide enhanced mechanical performance while affording improved radiologic monitoring. The anchor devices described herein can incorporate a region composed of bias ply or meshed material (e.g. polymer strand, or wire strand). The struts can be manufactured by laser cutting a nitinol tube as is known in the art. The tubular device can also be manufactured of a material including platinum, gold, palladium, rhenium, tantalum, tungsten, molybdenum, rhenium, nickel, cobalt, stainless steel, Nitinol, and alloys thereof.

The anchor devices described herein are particularly suited for use in percutaneous procedures or for use in arthroscopic procedures, including but not limited to rotator cuff surgery, tendon and ligament affixation or repair, prosthetic attachment, and the like. The anchor devices described herein can be used in any procedure in which it is desired to fix a suture or a soft tissue to a solid object.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An anchor device for attaching materials within bone, the anchor device comprising:
    a body having a distal end region, a proximal end region, and a plurality of struts extending between the distal end region to the proximal end region and at least partially surrounding an interior volume of the body; and
    an attachment feature positioned within the interior volume of the body and coupled near the distal end region, the attachment feature comprising a cleat element configured to secure material to the body, the cleat element comprising at least two suture anchor elements, each suture anchor element having an inner post and an aperture configured to allow material to extend through; and
    wherein upon removal of a constraint and after delivery of the anchor device into bone the body passively transitions from a constrained, delivery configuration that is radially contracted and axially elongated to a relaxed, deployment configuration that is radially expanded and axially shortened, and
    wherein applying tension to the material extending through the apertures of the at least two suture anchor elements forces the at least two suture anchor elements to pivot laterally outward relative to one another to a splayed configuration.

2. The anchor device of claim 1, wherein the material secured by the attachment feature to the anchor device is suture or cable material.

3. The anchor device of claim 1, wherein the material is further configured to be affixed to a soft tissue structure that is selected from the group consisting of tendon, ligament, and joint capsule.

4. The anchor device of claim 1, wherein the tension applied to the material is maintained by the at least two suture anchor elements wherein at least a part of the material passed through the apertures of the at least two suture anchor elements and wrapped around a common post formed by the inner posts of the at least two suture anchor elements resulting in a portion of the material overlapping another portion of the material.

5. The anchor device of claim 1, further comprising a penetrating tip coupled to the distal end region of the body.

6. The anchor device of claim 5, wherein the penetrating tip has a trephine, fluted or conically-tapered outer geometry to facilitate penetration of bone.

7. The anchor device of claim 1, wherein tensioning of the material approximates the distal end region and the proximal end region causing the plurality of struts to radially expand.

8. The anchor device of claim 1, wherein the proximal end region comprises a discontinuous outer wall defining a proximal opening to the interior volume of the body within which the material is disposed such that soft tissue affixed to the material is in direct contact with the bone.

9. The anchor device of claim 1, wherein the plurality of struts expand near the proximal end region to a greater degree than the plurality of struts expand near the distal end region.

10. The anchor device of claim 1, wherein the body is fabricated from a superelastic metal or polymer.

11. The anchor device of claim 1, wherein the constraint comprises a generally rigid tubular element.

12. The anchor device of claim 11, wherein the generally rigid tubular element comprises a slot to accommodate the material.

13. The anchor device of claim 11, wherein the constraint comprises a circumferential ring element.

14. The anchor device of claim 1, wherein the constraint includes a primary constraint and further comprises a secondary constraint, wherein the secondary constraint is positioned over at least a region of the primary constraint during storage of the anchor device.

15. A suture or soft tissue anchor device configured to employ a self-expanding device that is constrained prior to delivery, in a relatively reduced diameter and relatively extended length, with subsequent deployment and delivery within bone, where it expands to a relatively larger diameter with a relatively shortened length; in which suture material or cable attached to the soft tissue being approximated or secured to the bone anchor is affixed or otherwise associated with a distal terminus or an element associated with the distal terminus of the anchor, such that tension applied on the suture or cable results in a force that foreshortens the length and expands the diameter of the anchor, the device additionally comprising an attachment feature comprising a cleat element comprising at least two suture anchor elements, each suture anchor element having an inner post and an aperture configured to allow the suture material or cable extend through,
    wherein applying tension to the suture material or cable extending through the apertures of the at least two suture anchor elements forces the at least two suture anchor elements to pivot laterally outward relative to one another to a splayed configuration.

16. The device of claim 15, wherein the device is fabricated from a superelastic metal or polymer.

17. The device of claim 15, further comprising a distal tip that is conically tapered to facilitate penetration of bone.

18. The device of claim 17, wherein the distal tip is configured with trephine or fluted geometry to facilitate penetration of bone.

19. The device of claim 18, wherein sutures affixed to a soft tissue structure are passed through an aperture located distally within the device and delivered through a proximal aperture of the device for subsequent tensioning.

20. The device of claim 15, wherein a generally tubular configured primary confinement element is used to maintain the self-expanding device in its confined geometry prior to distal delivery out of the primary confinement element and into the bone.

21. The device of claim 20, wherein the primary confinement element has a slot to accommodate introduction of suture material attached to a soft tissue structure.

22. The device of claim 15, wherein a primary confinement element positioned over the self-expanding device during storage is removed after chilling the self-expanding device immediately or shortly prior to deployment within the bone.

23. The device of claim 22 wherein a secondary confinement element is positioned over the primary confinement element during ambient temperature storage and subsequently removed after chilling the self-expanding device immediately or shortly prior to deployment within the bone.

24. The device of claim 15, wherein the suture material or cable is passed through the apertures of the at least two suture anchor elements and wrapped around a common post formed by the inner posts of the at least two suture anchor elements.

* * * * *